United States Patent [19]

Bell

[11] Patent Number: 5,013,732

[45] Date of Patent: May 7, 1991

[54] 3-ARYLCARBONYL- AND 3-CYCLOALKYL-CARBONYL-1-AMINOALKYL-1H-INDOLES

[75] Inventor: Malcolm R. Bell, East Greenbush, N.Y.

[73] Assignee: Sterling Drug Inc., New York, N.Y.

[21] Appl. No.: 559,787

[22] Filed: Jul. 30, 1990

Related U.S. Application Data

[60] Division of Ser. No. 409,913, Sep. 20, 1989, which is a division of Ser. No. 255,305, Oct. 11, 1988, Pat. No. 4,885,295, which is a continuation of Ser. No. 928,335, Nov. 7, 1986, abandoned, which is a division of Ser. No. 810,942, Dec. 19, 1985, Pat. No. 4,634,776, which is a continuation of Ser. No. 755,239, Jul. 15, 1985, Pat. No. 4,581,354, which is a continuation-in-part of Ser. No. 637,931, Aug. 6, 1984, abandoned.

[51] Int. Cl.$^5$ .................. A61K 31/40; A61K 31/535; C07D 209/12; C07D 413/06

[52] U.S. Cl. .................. 514/210; 514/218; 514/228.2; 514/235.2; 514/253; 514/314; 514/316; 514/321; 514/323; 514/397; 514/414; 514/415; 514/419; 540/575; 544/58.2; 544/58.5; 544/58.6; 544/62; 544/121; 544/128; 544/129; 544/130; 544/139; 544/143; 544/144; 544/357

[58] Field of Search .............. 540/575; 544/129, 130, 544/121, 128, 139, 143, 144, 58.2, 58.5, 58.6, 62, 357, 360, 363, 370, 373; 546/168, 197, 187, 201; 548/336, 493, 454, 505, 465, 468; 514/210, 218, 228.2, 235.2, 253, 314, 316, 321, 323, 397, 415, 414, 419

[56] References Cited

U.S. PATENT DOCUMENTS

| | | | |
|---|---|---|---|
| 3,489,770 | 1/1970 | Herbst | 544/143 |
| 3,946,029 | 3/1976 | Descamps et al. | 544/131 |
| 4,229,464 | 10/1980 | Kampe et al. | 548/493 |

*Primary Examiner*—Robert W. Ramsuer
*Attorney, Agent, or Firm*—William G. Webb; Paul E. Dupont

[57] ABSTRACT

3-Arylcarbonyl- and 3-cycloalkylcarbonyl-1-aminoalkyl-1H-indoles, useful as analgesic, anti-rheumatic and anti-inflammatory agents, are prepared by reacting a 3-arylcarbonyl- or 3-cycloalkylcarbonylindole with an aminoalkyl halide in the presence of an acid-acceptor; by reacting a 1-aminoalkyl-1H-indole with an arylcarboxylic acid halide or a cycloalkanecarboxylic acid halide in the presence of a Lewis acid; or by reacting a 3-arylcarbonyl- or 3-cycloalkanecarbonyl-1-tosyloxyalkyl- or haloalkyl-1H-indole with an amine.

6 Claims, No Drawings

3-ARYLCARBONYL- AND 3-CYCLOALKYL-CARBONYL-1-AMINOALKYL-1H-INDOLES

RELATED APPLICATIONS

This is a division of my prior, copending application Ser. No. 409,913, filed Sept. 20, 1989, which is a division of application Ser. No. 25,305, filed Oct. 11, 1988, now U.S. Pat. No. 4,885,295, which is a continuation of my prior application Ser. No. 928,335, filed Nov. 7, 1986, now abandoned, which is a division of my prior application Ser. No. 810,942, filed Dec. 19, 1985, now U.S. Pat. No. 4,634,776, which is a continuation of my prior application Ser. No. 755,239, filed July 15, 1985, now U.S. Pat. No. 4,581,354, patented Apr. 8, 1986, which is a continuation-in-part of my prior application Ser. No. 637,931, filed Aug. 6, 1984, now abandoned.

BACKGROUND OF THE INVENTION (a) Field of the Invention

This invention relates to 3-arylcarbonyl- and 3-cycloalkylcarbonyl-1-aminoalkyl-1H-indoles which are useful as analgesic, anti-rheumatic and anti-inflammatory agents.

(b) Information Disclosure Statement

Deschamps et al. U.S. Pat. No. 3,946,029 discloses compounds having the formula:

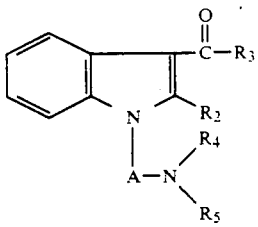

where, inter alia, A is alkylene; $R_2$ is one to four carbon alkyl; $R_3$ is a 2-, 3- or 4-pyridyl group; and $R_4$ and $R_5$ are joined together to form, with the nitrogen atom, a piperidino, pyrrolidino or morpholino group. The compounds are said to possess fibrinolytic and anti-inflammatory activities.

Essentially the same disclosure is found in Inion et al., Eur. J. of Med. Chem., 10 (3), 276–285 (1975). Specifically disclosed in both these references is the species, 2-isopropyl-3-(3-pyridylcarbonyl)-1-[2-(4-morpholinyl)ethyl]indole.

Herbst U.S. Pat. No. 3,489,770 generically discloses compounds having the formula:

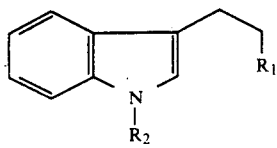

where, inter alia, $R_1$ is "diloweralkylamino, pyrrolidinyl, piperidino and morpholino and $R_2$ is ... cyclo(lower)alkanoyl and adamantanylcarbonyl". Although not within the ambit of the above-defined genus, the Herbst patent also discloses a variety of species where $R_2$ is an arylcarbonyl group. Specifically disclosed, for example, is the species "1-p-(chlorobenzoyl)-3-(2-morpholinoethyl)indole". The compounds are said to possess anti-inflammatory, hypotensive, hypoglycemic and CNS activities.

Tambute, Acad. Sci. Comp. Rend., Ser. C, 278 (20), 1239–1242 (1974) discloses compounds of the formula:

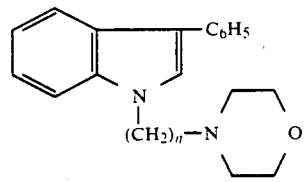

where n is 2 or 3. No utility for the compounds is given.

SUMMARY

In a composition of matter aspect, the invention relates to 2-$R_2$-3-$R_3$-carbonyl-1-aminoalkyl-1H-indoles and their acid-addition salts which are useful as analgesic, anti-rheumatic and anti-inflammatory agents.

In a second composition of matter aspect, the invention relates to 2-$R_2$-3-$R_3$-carbonylindoles useful as intermediates for the preparation of said 2-$R_2$-3-$R_3$-carbonyl-1-aminoalkyl-1H-indoles. Certain of the 2-$R_2$-3-$R_3$-carbonyl-indoles are also useful as anti-rheumatic agents.

In a third composition of matter aspect, the invention relates to 2-$R_2$-1-aminoalkyl-1H-indoles also useful as intermediates for the preparation of said 2-$R_2$-3-$R_3$-carbonyl-1-aminoalkyl-1H-indoles. Certain of the 2-$R_2$-1-aminoalkyl-1H-indoles are also useful as analgesics.

In a process aspect, the invention relates to a process for preparing 2-$R_2$-3-$R_3$-carbonyl-1-aminoalkyl-1H-indoles which comprises reacting a 2-$R_2$-3-$R_3$-carbonyl-indole with an aminoalkyl halide in the presence of an acid-acceptor.

In a second process aspect, the invention relates to a process for preparing 2-$R_2$-3-$R_3$-carbonyl-1-aminoalkyl-1H-indoles which comprises reacting a 2-$R_2$-1-aminoalkyl-1H-indole with an arylcarboxylic acid halide or a cycloalkanecarboxylic acid halide in the presence of a Lewis acid.

In a third process aspect, the invention relates to a process for preparing said 2-$R_2$-3-$R_3$-carbonyl-1-aminoalkyl-1H-indoles which comprises reacting a 2-$R_2$3-$R_3$-carbonyl-1-tosyloxyalkyl- or 1-haloalkyl-1H-indole with an amine.

In a method aspect, the invention relates to a method of use of the said 2-$R_2$-3-$R_3$-carbonyl-1-aminoalkyl-1H-indoles for the relief of pain or of rheumatic or inflammatory conditions.

In a second method aspect, the invention relates to a method of use of the said 2-$R_2$-3-$R_3$-carbonylindoles for the relief of rheumatic conditions.

In a third method aspect, the invention relates to a method of use of the said 2-$R_2$-1-aminoalkyl-1H-indoles for the relief of pain.

DETAILED DESCRIPTION OF THE PREFERRED EMBODIMENTS

More specifically, the invention relates to 2-$R_2$-3-$R_3$-carbonyl-1-aminoalkyl-1H-indoles, which are useful as analgesic, anti-rheumatic and anti-inflammatory agents, having the formula:

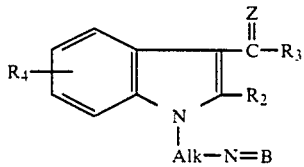

where:

R$_2$ is hydrogen, lower-alkyl, chloro, phenyl or benzyl (or phenyl or benzyl substituted by from one to two substituents selected from halo, lower-alkyl, lower-alkoxy, hydroxy, amino, lower-alkylmercapto, lower-alkylsulfinyl or lower-alkylsulfonyl);

R$_3$ is cyclohexyl, lower-alkoxycyclohexyl, phenyl (or phenyl substituted by from one to two substituents selected from halo, lower-alkoxy, hydroxy, benzyloxy, lower-alkyl, nitro, amino, lower-alkylamino, di-lower-alkylamino, lower-alkoxy-lower-alkylamino, lower-alkanoylamino, benzoylamino, trifluoroacetylamino, lower-alkyl-sulfonylamino, carbamylamino, lower-alkylmercapto, lower-alkylsulfinyl, lower-alkylsulfonyl, cyano, formyl or oximinomethylene), methylenedioxyphenyl, 3- or 4-hydroxy-1-piperidinylphenyl, 1-piperazinylphenyl, (1H-imidazol-1-yl)phenyl,(1-pyrrolyl)phenyl, aminomethylphenyl, guanidinylmethylphenyl, N-cyanoguanidinylmethylphenyl, styryl, lower-alkyl-substituted-styryl, fluoro-substituted-styryl, 2- or 4-biphenyl, 1- or 2-naphthyl (or 1- or 2-naphthyl substituted by from one to two substituents selected from lower-alkyl, lower-alkoxy, hydroxy, bromo, chloro, fluoro, lower-alkoxycarbonyl, carbamyl, cyano, lower-alkylmercapto, lower-alkylsulfinyl, lower-alkylsulfonyl or trifluoromethyl), thienyl, furyl, benzo[b]furyl, benzo[b]thienyl, quinolyl or (N-lower-alkyl)pyrrolyl;

R$_4$ is hydrogen or from one to two substituents selected from lower-alkyl, hydroxy, lower-alkoxy or halo in the 4-, 5-, 6- or 7- positions;

C=Z is C=O or C=NOH;

Alk is α,ω-lower-alkylene having the formula (CH$_2$)$_n$, where n is an integer from 2 to 6, or such lower-alkylene substituted on the α- or the ω-carbon atom by a lower-alkyl group; and N=B is azido, amino, N-lower-alkylamino, N,N-di-lower-alkylamino, N-(hydroxy-lower-alkyl)amino, N,N-di-(hydroxy-lower-alkyl)amino, N-lower-alkyl-N-(hydroxy-lower-alkyl)amino, N-(lower-alkoxy-lower-alkyl)amino, N-(halo-n-propyl)amino, 4-morpholinyl, 2-lower-alkyl-4-morpholinyl, 2,6-di-lower-alkyl-4-morpholinyl, 4-thiomorpholinyl, 4-thiomorpholinyl-S-oxide, 4-thiomorpholinyl-S,S-dioxide, 1-piperidinyl, 3- or 4-hydroxy-1-piperidinyl, 3- or 4-lower-alkanoyloxy-1-piperidinyl, 3- or 4-amino-1-piperidinyl, 3- or 4-(N-lower-alkanoylamino)-1-piperidinyl, 2-cyclohexylmethyl-1-piperidinyl, 1-pyrrolidinyl, 3-hydroxy-1-pyrrolidinyl, 1-azetidinyl, 1-piperazinyl, 4-lower-alkyl-1-piperazinyl, 4-lower-alkanoyl-1-piperazinyl, 4-carbolower-alkoxy-1-piperazinyl, hexahydro-4H-1,4-diazepin-4-yl or the N=B N-oxides thereof.

Preferred compounds of formula I above are those where:

R$_2$ is hydrogen or lower-alkyl;

R$_3$ is phenyl, chlorophenyl, fluorophenyl, dichlorophenyl, difluorophenyl, lower-alkoxyphenyl, di-lower-alkoxyphenyl, hydroxyphenyl, lower-alkylphenyl, aminophenyl, lower-alkylaminophenyl, lower-alkanoylaminophenyl, benzoylaminophenyl, trifluoroacetylaminophenyl, lower-alkylmercaptophenyl, lower-alkylsulfinylphenyl, lower-alkylsulfonylphenyl, cyanophenyl, aminomethylphenyl, styryl, 2- or 4-biphenyl, 1-or 2-naphthyl (or 1- or 2-naphthyl substituted by lower-alkyl, lower-alkoxy, hydroxy, bromo, chloro or fluoro), 2-thienyl, 2-, 3-, 4- or 5-benzo[b]furyl, 2-, 3-, 4- or 5-benzo[b]thienyl or 2- or 3-(N-lower-alkyl)pyrrolyl;

R$_4$ is hydrogen or lower-alkyl, lower-alkoxy, fluoro or chloro in the 4-, 5-, 6- or 7-positions;

C=Z is C=0;

Alk is 1,2-ethylene (-CH$_2$CH$_2$-), 1-lower-alkyl-1, 2-ethylene (CHRCH$_2$-), 2-lower-alkyl-1,2-ethylene (-CH$_2$CHR-), where R is lower-alkyl, 1,3-propylene (-CH$_2$CH$_2$CH$_2$-) or 1,4-butylene; and N=B is 4-morpholinyl, 3- or 4-hydroxy-1-piperidinyl, 1-pyrrolidinyl, 3-hydroxy-1-pyrrolidinyl, N-lower-alkylamino, N,N-di-lower-alkylamino, N,N-di-(hydroxy-lower-alkyl)amino, 1-piperazinyl, 4-lower-alkyl-1-piperazinyl or 4-lower-alkanoyl-1-piperazinyl.

Particularly preferred compounds of formula I within the ambit of the invention as defined above are those where:

R$_2$ is hydrogen or lower-alkyl;

R$_3$ is phenyl, chlorophenyl, fluorophenyl, difluorophenyl, lower-alkoxyphenyl, lower-alkyl-phenyl, aminophenyl, lower-alkylaminophenyl, lower alkanoylaminophenyl, trifluoroacetylaminophenyl, lower-alkylmercaptophenyl, lower-alkylsulfinylphenyl, aminomethylphenyl, 1- or 2-naphthyl (or 1- or 2-naphthyl substituted by lower-alkyl, lower-alkoxy, hydroxy, bromo, chloro or fluoro), 2-thienyl, 2-, 3-, 4- or 5-benzo[b]furyl or 2-, 3-, 4- or 5-benzo[b]thienyl;

R$_4$ is hydrogen, lower alkoxy, fluoro or chloro in the 4-, 5-, 6- or 7-positions;

C=Z is C=0;

Alk is 1,2-ethylene, 2-lower-alkyl-1,2-ethylene, 1-lower-alkyl-1,2-ethylene, 1,3-propylene or 1,4-butylene; and N=B is 4-morpholinyl, 3- or 4-hydroxy-1-piperidinyl, 1-pyrrolidinyl, 3-hydroxy-1-pyrrolidinyl, N,N-di-lower-alkylamino, N,N-di-(hydroxy-lower-alkyl)amino, 1-piperazinyl or 4-lower-alkyl-1-piperazinyl.

Other preferred compounds of formula I within the ambit of the invention as defined above are those where:

R$_2$ is hydrogen or lower-alkyl;

R$_3$ is phenyl, fluorophenyl, chlorophenyl, dichlorophenyl, lower-alkoxyphenyl, di-lower-alkoxyphenyl, hydroxyphenyl, lower-alkanoylaminophenyl, benzoylaminophenyl, lower-alkylsulfonylphenyl, cyanophenyl, styryl, 1-naphthyl, lower-alkoxy-substituted-1- or 2-naphthyl, 3-benzo[b]thienyl or 2- or 3-(N-lower-alkyl)pyrrolyl;

R$_4$ is hydrogen or lower-alkyl, lower-alkoxy, fluoro or chloro in the 4-, 5-, 6- or 7-positions;

C=Z is C=0;

Alk is 1,2-ethylene, 1-lower-alkyl-1,2-ethylene, 2-lower-alkyl-1,2-ethylene, 1,3-propyllene or 1,4-butylene; and N=B is 4-morpholinyl or 1-pyrrolidinyl.

Still other preferred compounds of formula I within the ambit of the invention as defined above are those where:

R$_2$ is hydrogen, lower-alkyl or phenyl;

R$_3$ is cyclohexyl, lower-alkoxycyclohexyl, phenyl, fluorophenyl, lower-alkoxyphenyl, lower-alkoxyfluorophenyl, benzyloxyphenyl, methylenedioxyphenyl, lower-alkylphenyl, di-lower-alkylphenyl, lower-alkylsulfonylaminophenyl, carbamylaminophenyl, cyanophenyl, formylphenyl, oximinomethylenephenyl, (1-pyrrolyl)phenyl, guanidinylmethylphenyl, N-cyanoguanidinylmethylphenyl, 2-naphthyl, 2-furyl or 2-benzo[b]thienyl;

$R_4$ is hydrogen or lower-alkyl, hydroxy or lower-alkoxy in the 4-, 5-, 6- or 7-positions;

C=Z is C=O or C=NOH;

Alk is 1,2-ethylene or 1-lower-alkyl-1,2-ethylene; and

N=B is 4-morpholinyl, 1-piperidinyl or 1-pyrrolidinyl or the N-oxides thereof.

Also considered to be within the ambit of the invention are species having the formulas Ia and Ib:

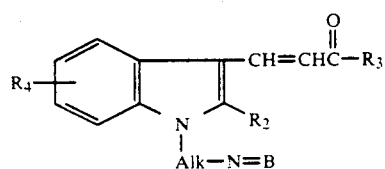

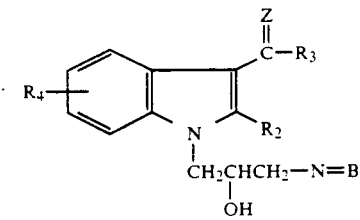

where $R_2$, $R_3$, $R_4$, Alk, Z and N=B have the meanings given above.

As used herein, unless specifically defined otherwise, the terms lower-alkyl, lower-alkoxy and lower-alkanoyl mean monovalent, aliphatic radicals, including branched chain radicals, of from one to about four carbon atoms, for example, methyl, ethyl, propyl, isopropyl, butyl, sec.-butyl, methoxy, ethoxy, propoxy, isopropoxy, butoxy, sec.-butoxy, formyl, acetyl, propionyl, butyryl and isobutyryl.

As used herein, the term cycloalkyl means saturated alicyclic groups having from three to seven ring carbon atoms, including cyclopropyl, cyclobutyl, cyclopentyl, cyclohexyl and cycloheptyl.

As used herein, the term halo means fluoro, chloro or bromo.

In one method, the compounds of formula I where C=Z is C=O are prepared by reacting a 2-$R_2$-3-$R_3$-carbonyl-1H-indole of formula II with an amino-lower-alky halide in the presence of an acid-acceptor:

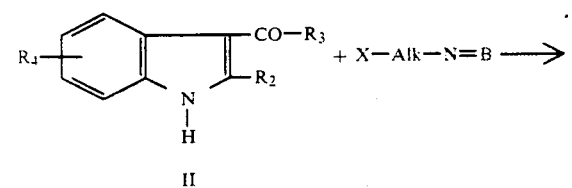

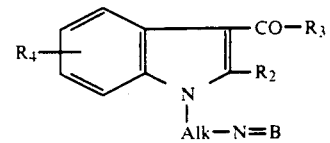

(C=Z is C=O)

where $R_2$, $R_3$, $R_4$, Alk and N=B have the meanings given above and X represents halogen. The reaction is preferably carried out in an organic solvent inert under the conditions of the reaction such as dimethylformamide (hereinafter DMF), dimethylsulfoxide (hereinafter DMSO), a lower-alkanol or acetonitrile. Suitable acid-acceptors are an alkali metal carbonate, such as sodium carbonate or potassium carbonate, or an alkali metal hydride, such as sodium hydride, an alkali metal amide, such as sodamide, or an alkali metal hydroxide, such as potassium hydroxide. Preferred solvents are DMF and DMSO, and preferred acid-acceptors are sodium hydride, potassium carbonate and potassium hydroxide. The reaction is carried out at a temperature in the range from around 0° C. to the boiling point of the solvent used.

The 2-$R_2$-3-$R_3$-carbonyl-1H-indoles of formula II are in turn prepared by reacting a 2-$R_2$-indole with a lower-alkyl magnesium halide and reacting the resulting Grignard with an appropriate $R_3$-carboxylic acid halide. The reaction is carried out in an organic solvent inert under the conditions of the reaction, such as dimethyl ether, dioxane or tetrahydrofuran (hereinafter THF), at a temperature in the range from −5° C. to the boiling point of the solvent used.

Certain compounds within the ambit of formula II, namely those of formula II':

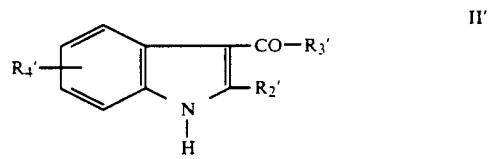

where $R_2'$ is hydrogen, lower-alkyl or phenyl; $R_3'$ is fluorophenyl, difluorophenyl, lower-alkoxyphenyl, di-loweralkoxyphenyl, lower-alkoxy-fluorophenyl, methylenedioxyphenyl, aminophenyl, cyanophenyl, 2- or 4-biphenyl, 1- or 2- naphthyl or lower-alkoxy-substituted-1- or 2-naphthyl; and $R_4'$ is hydrogen or fluoro are novel species and comprise a further composition aspect of this invention.

In another method, the compounds of formula I where C=Z is C=O are prepared by reacting a 2-$R_2$-1-aminoalkyl-1H-indole of formula III with an appropriate $R_3$-carboxylic acid halide ($R_3$-CO-X) in the presence of a Lewis acid, such as aluminum chloride, and in an organic solvent inert under the conditions of the reaction. Suitable solvents are chlorinated hydrocarbons such as methylene dichloride (hereinafter MDC) or ethylene dichloride (hereinafter EDC). The reaction is carried out at a temperature from 0° C. to the boiling point of the solvent used. The method is illustrated by the reaction:

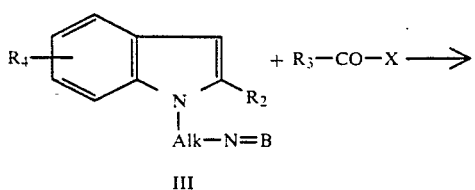

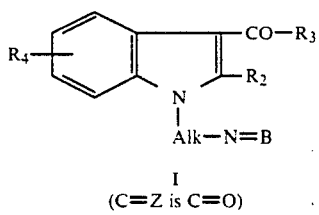

where $R_2$, $R_3$, $R_4$, Alk, N=B and X have the meanings given above.

The intermediate 2-$R_2$-1-aminoalkyl-1H-indoles of formula III wherein $R_2$, $R_4$, Alk and N=B have the previously given meanings comprise yet a further composition aspect of the present invention. These compounds are prepared by one of two methods. In one method, a 2-$R_2$-indole of formula IV is reacted with an amino-lower-alkyl halide in the presence of an acid-acceptor, in an organic solvent inert under the conditions of the reaction using the same conditions described above for the preparation of the compounds of formula I by alkylation of the compounds of formula II.

In a second method, a 2-$R_2$-indole of formula IV is reacted with a halo-lower-alkanamide in the presence of a strong base, and the resulting 2-$R_2$-1H-indole-1-alkanamide of formula V is then reduced with lithium aluminum hydride. The reaction of the 2-$R_2$-indole of formula IV with the halo-lower-alkanamide is carried out in an appropriate organic solvent, such as DMF, at a temperature from −5° C. to about 50° C. The reduction of the amides of formula V with lithium aluminum hydride is carried out in an inert organic solvent, such as diethyl ether, THF or dioxane, at a temperature from −5° C. to about 50° C. The two methods are illustrated by the following reaction sequence:

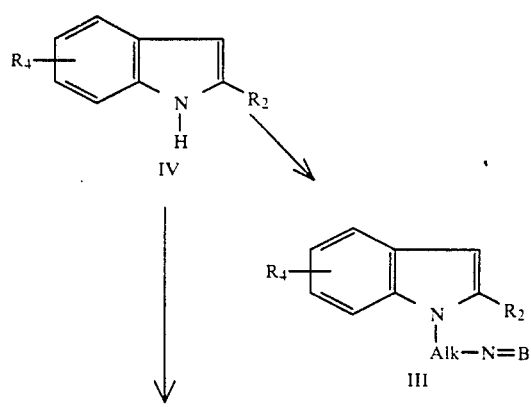

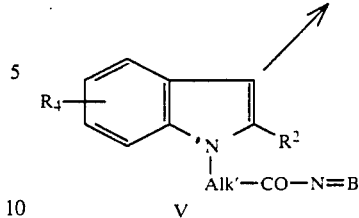

where $R_2$, $R_4$, Alk and N=B have the meanings given above, and Alk' is lower-alkylene having the formula $(CH_2)_{n'}$, where n' is an integer from 1 to 5 or such lower-alkylene group substituted on the ω-carbon atom by a lower-alkyl group.

In another method for preparing the compounds of formula I where C=Z is C=O, a 2-$R_2$-3-$R_3$-carbonyl-1(2-tosyloxy-lower-alkyl)- or (2-halo-lower-alkyl)-1H-indole of formula VI is reacted with a molar equivalent amount of an amine, H-N=B, in an organic solvent inert under the conditions of the reaction, such as acetonitrile, a lower-alkanol or DMF. The reaction is preferably carried out by heating a solution of the reactants at the boiling point of the mixture. The method is illustrated by the reaction:

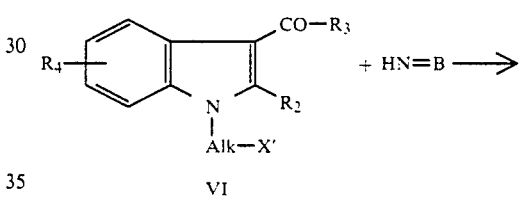

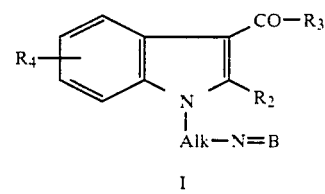

where $R_2$, $R_3$, $R_4$ and N=B have the meanings given above, and X' represents a toluenesulfonyl or halo group.

The 2-$R_2$-3-$R_3$-carbonyl-1-(2-tosyloxy-lower-alkyl) or 1-(2-halo-lower-alkyl)-1H-indoles of formula VI, where Alk is 1,2-ethylene, are in turn prepared by reaction of a 2-$R_2$-3-$R_3$-carbonyl indole of formula II with a lower-alkyl lithium, for example n-butyl lithium, in an inert organic solvent, such as THF, dioxane or diethyl ether, followed by reaction of the resulting lithium salt with ethylene oxide. Reaction of the resulting 2-$R_2$-3-$R_3$-carbonyl-1-(2-hydroxyethyl)-1H-indole with toluenesulfonyl chloride in the presence of an acid-acceptor affords the 1-(2-tosyloxyethyl)-1H-indoles, while reaction of the product with a phosphorus trihalide affords the corresponding 1-(2-haloethyl)-1H-indoles.

The 2-$R_2$-3-$R_3$-carbonyl-1-(2-halo-lower-alkyl)-1H-indoles of formula VI, where Alk has the other possible meanings, are prepared by reaction of a 2-$R_2$-3-$R_3$-carbonyl indole of formula II with an α,ω-dihalo-lower-alkane in the presence of a strong base, such as sodium hydride in an inert organic solvent, such as DMF. The reaction generally occurs at ambient temperature.

The compounds of formula Ia are prepared by reaction of a 2-R$_2$-3-formyl-1-aminoalkyl-1H-indole with an appropriate methyl R$_3$ ketone according to the reaction:

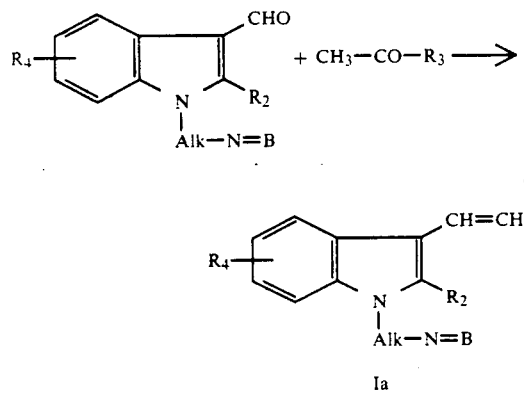

where R$_2$, R$_3$, R$_4$, Alk and N=B have the meanings given above. The reaction is carried out in the presence of a mineral acid and in an organic solvent inert under the conditions of the reaction. Preferred solvents are lower alkanols, such as methanol or ethanol.

The compounds of formula Ib, where Z is C=O, are prepared by reaction of a 2-R$_2$-3-R$_3$-carbonylindole of formula II with an epihalohydrin in the presence of a strong base, such as an alkali metal hydride, in an inert solvent, such as DMF or DMSO, and reaction of the resulting 2-R$_2$-3-R$_3$-carbonyl-1-[1-(2,3-epoxy)propyl]-1H-indole with an appropriate amine, H—N=B, according to the reactions:

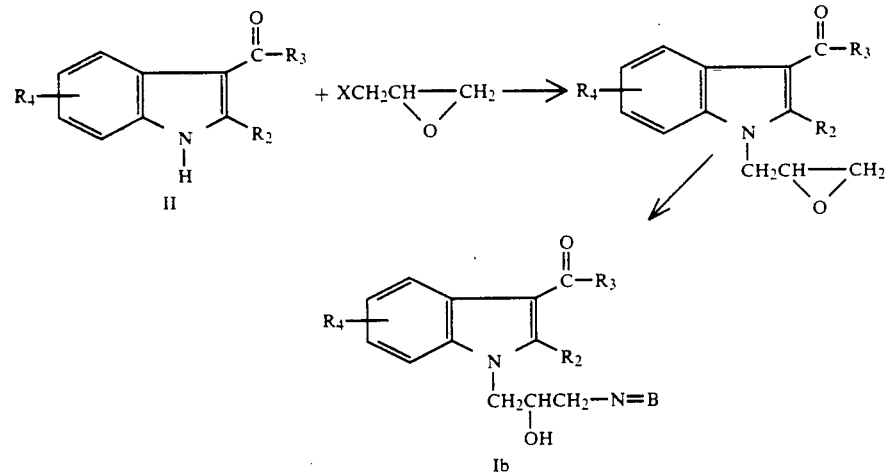

where R$_2$, R$_3$, R$_4$, Alk and N=B have the meanings given above.

Another method for preparing the compounds of formula I where R$_4$ is 5-hydroxy and C=Z is C=O comprises reacting benzoquinone with an appropriate N-(Alk-N=B)-N-(1-R$_2$-3-oxo-3-R$_3$-propenyl)amine of formula VII in an inert, water immiscible organic solvent, such as nitromethane. The N-(N=B-alkyl)-N-(1-R$_2$-3-oxo-3-R$_3$-propenyl)amine in turn is prepared by reaction of a 1,3-diketone, R$_2$COCH$_2$COR$_3$, with an appropriate aminoalkylamine, B=N-Alk-NH$_2$ under dehydrating conditions. The reaction is preferably carried out by heating a solution of the reactants in an inert, water immiscible solvent under a Dean-Stark trap. The method is represented by the reaction sequence:

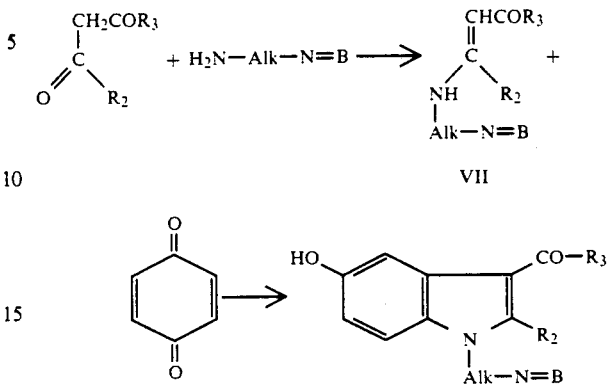

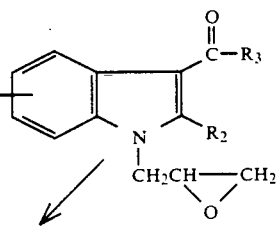 

By further chemical manipulations of various functional groups in the compounds of formulas I, Ia and Ib prepared by one or more of the above-described methods, other compounds within the ambit of the invention can be prepared. For example the compounds where R$_3$ is aminophenyl are advantageously prepared from the corresponding species where R$_3$ is nitrophenyl by reduction of the latter.

The reduction can be carried out either catalytically with hydrogen, for example over a platinum oxide catalyst at ambient temperature and in an appropriate organic solvent, such as a lower-alkanol, ethyl acetate or acetic acid or mixtures thereof, at hydrogen pressures from around 30 to 60 p.s.i.g., or alternatively the reduction can be carried out chemically, for example with iron in the presence of hydrochloric acid in an appropriate organic solvent, for example a lower-alkanol. The reaction is carried out at temperatures from ambient to the boiling point of the solvent used for the reaction.

The aminophenyl compounds thus prepared can then be acylated or sulfonylated to prepare compounds where R$_3$ is lower-alkanoylaminophenyl, benzoylaminophenyl, trifluoroacetylaminophenyl or lower-alkylsulfonylaminophenyl by reaction of an appropriate acid anhydride or acid halide with the corresponding species where R$_3$ is aminophenyl. It is advantageous, although not essential, to carry out the reaction in the presence of an acid acceptor, such as an alkali metal carbonate, for example potassium carbonate, or a tri-lower-alkylamine, such as trimethylamine or triethylamine. The reaction is carried out in an inert organic solvent at a temperature in the range from −5° C. to around 80° C. Suitable solvents are acetic acid, MDC, EDC or toluene.

Other simple chemical transformations which are entirely conventional and well known to those skilled in the art of chemistry and which can be used for effecting changes in functional groups attached to the $R_3$-carbonyl group, $(C=O)R_3$, involve cleavage of aryl ether functions, for example with aqueous alkali or a pyridine hydrohalide salt to produce the corresponding phenolic compound ($R_3$ is hydroxyphenyl); preparation of compounds where $R_3$ is phenyl substituted by a variety of amine functions by reaction of the corresponding halophenyl species with an appropriate amine; catalytic debenzylation of benzyloxy-substituted species to prepare the corresponding phenolic compound ($R_3$ is hydroxyphenyl); catalytic reduction of a nitrile function to produce the corresponding aminomethyl-substituted species ($R_3$ is aminomethylphenyl); saponification of amide groups to produce the corresponding amino compounds; acylation of hydroxy-substituted species to produce the corresponding esters; acylation of amino-substituted species to prepare the corresponding amides; oxidation of sulfides to prepare either the corresponding S-oxides or S,S-dioxides; reductive alkylation of amino-substituted species to prepare the corresponding mono- or di-loweralkylamino substituted species; reaction of amino-substituted species with an alkali metal isocyanate to prepare the corresponding carbamylamino-substituted species ($R_3$ is carbamylaminophenyl); reaction of an aminomethyl-substituted species with a di-lower-alkylcyanocarbonimidodithioate and reaction of the resulting product with ammonia to prepare the corresponding N-cyanoguanidinylmethyl-substituted species ($R_3$ is cyanoguanidinylmethylphenyl); reduction of a cyano-substituted species with sodium hypophosphite to prepare a corresponding formyl-substituted compound ($R_3$ is formylphenyl); reaction of a formylphenyl species or a $R_3$-carbonyl species with hydroxylamine to prepare the corresponding oximino methylenephenyl-substituted species ($R_3$ is oximinomethylenephenyl) or the $R_3$-carbonyl oximes ($C=Z$ is $C=NOH$); reaction of an aminophenyl species with a 2,5-di-loweralkoxytetrahydrofuran to prepare a (1-pyrrolyl)phenyl substituted species ($R_3$ is 1-pyrrolylphenyl); oxidation of the $N=B$ function, for example by fermentative procedures, to prepare the corresponding N-oxides; or reaction of a 1-aminoalkyl-1H-indole of formula III where $R_2$ is hydrogen with hexamethylenephosphoramide followed by a lower-alkyl halide to prepare the corresponding compounds of formula III where $R_2$ is lower-alkyl.

The compounds of formulas I, Ia, Ib and III in free base form are converted to the acid-addition salt form by interaction of the base with an acid. In like manner, the free base can be regenerated from the acid-addition salt form in conventional manner, that is by treating the salts with cold, weak aqueous bases, for example alkali metal carbonates and alkali metal bicarbonates. The bases thus regenerated can be interacted with the same or a different acid to give back the same or a different acid-addition salt. Thus the novel bases and all of their acid-addition salts are readily interconvertible.

It will thus be appreciated that formulas I, Ia, Ib and III not only represent the structural configuration of the bases of formulas I, Ia, Ib and III but are also representative of the structural entities which are common to all of the compounds of formulas I, Ia, Ib and III, whether in the form of the free base or in the form of the acid-addition salts of the base. It has been found that, by virtue of these common structural entities the bases of formulas I, Ia and Ib, and certain of the bases of formula III, and their acid-addition salts have inherent pharmacological activity of a type to be more fully described hereinbelow. This inherent pharmacological activity can be enjoyed in useful form for pharmaceutical purposes by employing the free bases themselves or the acid-addition salts formed from pharmaceutically acceptable acids, that is acids whose anions are innocuous to the animal organism in effective doses of the salts so that beneficial properties inherent in the common structural entity represented by the free bases are not vitiated by side effects ascribable to the anions.

In utilizing this pharmacological activity of the salts of the invention, it is preferred, of course, to use pharmaceutically acceptable salts. Although water insolubility, high toxicity or lack of crystalline character may make some particular salt species unsuitable or less desirable for use as such in a given pharmaceutical application, the water-insoluble or toxic salts can be converted to the corresponding pharmaceutically acceptable bases by decomposition of the salts with aqueous base as explained above, or alternatively they can be converted to any desired pharmaceutically acceptable acid-addition salt by double decomposition reactions involving the anion, for example by ion-exchange procedures.

Moreover, apart from their usefulness in pharmaceutical applications, the salts are useful as characterizing or identifying derivatives of the free bases or in isolation or purification procedures. Like all of the acid-addition salts, such characterizing or purification salt derivatives can, if desired, be used to regenerate the pharmaceutically acceptable free bases by reaction of the salts with aqueous base, or alternatively they can be converted to a pharmaceutically acceptable acid-addition salt by, for example, ion-exhange procedures.

The novel feature of the compounds of the invention, then, resides in the concept of the bases and cationic forms of the new 2-$R_2$-3-$R_3$-carbonyl-1-aminoalkyl-1H-indoles of formulas I, Ia and Ib and the 2-$R_2$-1-aminoalkyl-1H-indoles of formula III and not in any particular acid moiety or acid anion associated with the salt forms of the compounds; rather, the acid moieties or anions which can be associated with the salt forms are in themselves neither novel nor critical and therefore can be any acid anion or acid-like substance capable of salt formation with the bases.

Thus appropriate acid-addition salts are those derived from such diverse acids as formic acid, acetic acid, isobutyric acid, alpha-mercaptopropionic acid, malic acid, fumaric acid, succinic acid, succinamic acid, tartaric acid, citric acid, lactic acid, benzoic acid, 4-methoxybenzoic acid, phthalic acid, anthranilic acid, 1-naphthalenecarboxylic acid, cinnamic acid, cyclohexanecarboxylic acid, mandelic acid, tropic acid, crotonic acid, acetylenedicarboxylic acid, sorbic acid, 2-furancarboxylic acid, cholic acid, pyrenecarboxylic acid, 2-pyridinecarboxylic acid, 3-indoleacetic acid, quinic acid, sulfamic acid, methanesulfonic acid, isethionic acid, benzenesulfonic acid, p-toluenesulfonic acid, benzenesulfinic acid, butylarsonic acid, diethylphosphonic acid, p-aminophenylarsinic acid, phenylstibnic acid, phenylphosphinous acid, methylphosphinic acid, phenylphosphinic acid, hydrofluoric acid, hydrochloric acid, hydrobromic acid, hydriodic acid, perchloric acid, nitric acid, sulfuric acid, phosphoric acid, hydrocyanic acid, phosphotungstic acid, molybdic acid, phosphomolybdic acid, pyrophosphoric acid, arsenic acid, picric acid, picrolonic acid, barbituric acid, boron trifluoride and the like.

The acid-addition salts are prepared by reacting the free base and the acid in an organic solvent and isolating the salt directly or by concentration of the solution.

In standard pharmacological test procedures, the compounds of formulas I, Ia and Ib have been found to possess analgesic, anti-rheumatic and anti-inflammatory activities and are thus useful as analgesic, anti-rheumatic and anti-inflammatory agents. Certain of the compounds of formula II have been found to possess anti-rheumatic activity, and certain of the compounds of formula III have been found to possess analgesic activity, thus indicating usefulness of those species as anti-rheumatic and analgesic agents, respectively.

The test procedures used to determine the analgesic activities of the compounds have been described in detail in the prior art and are as follows: The acetylcholine-induced abdominal constriction test, which is a primary analgesic screening test designed to measure the ability of a test agent to suppress acetylcholine-induced abdominal constriction in mice, described by Collier et al., Brit. J. Pharmacol. Chemotherap. 32, 295 (1968); a modification of the anti-bradykinin test, which is also a primary analgesic screening procedure, described by Berkowitz et al., J. Pharmacol. Exptl. Therap. 177, 500–508 (1971), Blane et al., J. Pharm. Pharmacol. 19, 367–373 (1967), Botha et al., Eur. J. Pharmacol. 6, 312–321 (1969) and Deffenu et al., J. Pharm. Pharmacol. 18, 135 (1966); and the rat paw flexion test, described by Kuzuna et al., Chem. Pharm. Bull., 23, 1184–1191 (1975), Winter et al., J. Pharm. Exptl. Therap., 211, 678–685 (1979) and Capetola et al., J. Pharm. Exptl. Therap. 214, 16–23 (1980).

Anti-rheumatic and anti-inflammatory activities of the compounds of the invention were determined using the developing adjuvant arthritis assay in rats, the plasma fibronectin assay in arthritic rats and the pleurisy macrophage assay in rats. The developing adjuvant arthritis assay was used in conjunction with the plasma fibronectin assay as a primary screening method in the evaluation of compounds for potential use as disease modifying anti-rheumatic drugs. The procedure used to induce arthritis in rats is a modification of the methods published by Pearson, J. Chron. Dis. 16, 863–874 (1973) and by Glenn et al., Amer. J. Vet. Res. 1180–1193 (1965). The adjuvant induced arthritis bears many of the traits of rheumatoid arthritis. It is a chronic, progressive, deforming arthritis of the peripheral joints, with a primary mononuclear cell response consisting of bone and joint space invasion by pannus. In order to detect disease modifying anti-rheumatic drug activity, drug treatment is started before the disease has become irrevocably established. Since such drugs are not designed to be administered prophylactically, drug treatment of adjuvant arthritis is initiated at a time when the disease is developing but is not yet irreversible. Animals develop significant systemic arthritic disease which can be measured by swelling of the non-injected rear paw (NIP) 15 to 20 days following an initial injection on day 1 of complete Freund's adjuvant into the right hindfoot paw.

The important role played by fibronectin in arthritis has been evidenced by clinical [Scott et al., Ann. Rheum. Dis. 40, 142 (1981)]as well as experimental [Weissmann, J. Lab. Clin. Med. 100, 322 (1982)]studies. Plasma fibronectin measurements are made using the technique of rocket immuno-electrophoresis. Fibronectin levels in the arthritic rat are significantly higher than in normal animals. Nonsteroidal, anti-inflammatory drugs have no influence on the enhanced fibronectin levels seen in arthritic rats, while disease modifying anti-rheumatic drugs cause a significant decrease in plasma fibronectin.

The pleurisy macrophage assay is designed to define anti-arthritic drugs which inhibit macrophage accumulation in the pleural cavity following injection of an inflammatory stimulus. Standard disease modifying antirheumatic drugs are active in this assay while non-steroidal anti-inflammatory drugs are not. The activity of species in the pleurisy macrophage model thus indicates disease modifying anti-rheumatic drug activity. The macrophage is the characteristic cell type in chronic inflammatory responses in the rheumatoid synovium as well as other sites. When activated, macrophages produce a large variety of secretory products, including neutral proteases which play a destructive role in arthritis [Ackerman et al., J. Pharmacol. Exp. Thera. 215, 588 (1980)]. The in vivo model of inflammatory cell accumulation in the rat pleural cavity permits quantitation and differentiation of the accumulated cells. The cellular components are similar to those seen in the inflamed synovium. It has been hypothesized that drugs which are effective inhibitors of pleurisy macrophage activity may also be effective in slowing or reversing progression of arthritic disease (Ackerman supra), and the procedure used is a modification of the method published by Ackerman et al.

The compounds of formulas I, Ia, Ib, II and III of the invention can be prepared for pharmaceutical use by incorporating them in unit dosage form as tablets or capsules for oral or parenteral administration either alone or in combination with suitable adjuvants such as calcium carbonate, starch, lactose, talc, magnesium stearate, gum acacia and the like. Still further, the compounds can be formulated for oral or parenteral administration either in aqueous solutions of the water soluble salts or in aqueous alcohol, glycol or oil solutions or oil-water emulsions in the same manner as conventional medicinal substances are prepared.

The percentages of active component in such compositions may be varied so that a suitable dosage is obtained. The dosage administered to a particular patient is variable, depending upon the clinician's judgment using as criteria: the route of administration, the duration of treatment, the size and physical condition of the patient, the potency of the active component and the patient's response thereto. An effective dosage amount of the active component can thus only be determined by the clinician after a consideration of all criteria and using his best judgment on the patient's behalf.

The molecular structures of the compounds of the invention were assigned on the basis of study of their infrared, ultraviolet and NMR spectra. The structures were confirmed by the correspondence between calculated and found values for elementary analyses for the elements.

The following examples will further illustrate the invention without, however, limiting it thereto. All melting points are uncorrected.

EXEMPLARY DISCLOSURE

Preparation of Intermediates

A. The Compounds of Formula II

Preparation 1A

To a solution of 0.05 mole of methyl magnesium bromide in about 45 ml. of anhydrous diethyl ether at 0° C. under a nitrogen atmosphere was added, dropwise, a solution containing 6.0 g. (0.04 mole) of 2,7-dimethylindole in 30 ml. of anhydrous ether. When addition was complete, the reaction mixture was stirred at room temperature for one hour, then cooled in an ice bath and treated dropwise with a solution of 8.53 g. (0.05 mole) of 4-methoxybenzoyl chloride in 20 ml. of anhydrous ether. The mixture was stirred at room temperature for approximately twelve hours, then on a steam bath for two hours and then treated with ice water. Excess ammonium chloride was added, and the ether layer was separated, dried and evaporated to dryness to give a solid which was collected by filtration and washed thoroughly with water and ether to give 8.5 g. (76%) of 2,7-dimethyl-3-(4-methoxybenzoyl)indole, m.p. 182°–184° C.

Preparations 1B–1AU

Following a procedure similar to that described above in Preparation 1A, substituting for the 2,7-dimethylindole and the 4-methoxybenzoyl chloride used therein an appropriate 2-$R_2$-$R_4$-indole and an appropriate aroylchloride ($R_3$CO-Cl), the following species of formula II listed in Table A were prepared. In some instances the products, without further purification, were used directly in the next step of the synthesis of the final products of formula I, and no melting points were taken. In a few cases, the weight of the products was not obtained, and so calculation of yields of products in those instances are not possible. Here and elsewhere in the tables included with this specification, the melting point of the product (in ° C.) and the recrystallization solvent are given in columns headed "m.p./Solv.", and the yield, in percent, of product is given in columns headed "Yield".

TABLE A

| Prepn. | $R_2$ | $R_3$ | $R_4$ | m.p./Solv. | Yield |
|---|---|---|---|---|---|
| 1B | $CH_3$ | 4-$CH_3C_6H_4$ | — | 215-217/DMF-$H_2O$ | 85 |
| 1C | $CH_3$ | 2-furyl | — | | 98 |
| 1D | $CH_3$ | 4-$CH_3SC_6H_4$ | — | | |
| 1E | $CH_3$ | 4-$NO_2C_6H_4$ | — | | 23 |
| 1F | $CH_3$ | 4-$CH_3OC_6H_4$ | 5-F | 199-202/i-PrOH | |
| 1G | $CH_3$ | 4-$CH_3OC_6H_4$ | 7-F | 204-205/$H_2O$ | 42 |
| 1H | $CH_3$ | 4-$CH_3OC_6H_4$ | 7-$CH_3O$ | | 68 |
| 1-I | $CH_3$ | 4-$CH_3OC_6H_4$ | 5-/7-F(a) | | 55 |
| 1J | $CH_3$ | 4-$FC_6H_4$ | — | 199-201/EtOH | 38 |
| 1K | $CH_3$ | 3,4-$OCH_2OC_6H_3$ | — | 210-213/i-PrOH | 60 |
| 1L | $CH_3$ | 3-benzo[b]thienyl | — | 181-183 | 64 |
| 1M | $CH_3$ | 2-benzo[b]furyl | — | 220-220/i-PrOH | 75 |
| 1N | $CH_3$ | 2-$CH_3OC_6H_4$ | — | 203-206/i-PrOH | 75 |
| 1-O | $CH_3$ | 3-F-4-$CH_3OC_6H_3$ | — | 160-165/EtOH | 39 |
| 1P | $CH_3$ | 2-naphthyl | — | 208-213/i-PrOH | 57 |
| 1Q | H | 4-$CH_3OC_6H_4$ | 5-$CH_3$ | 189-192/EtOH | 42 |
| 1R | $CH_3$ | 3-$FC_6H_4$ | — | | 64 |
| 1S | $CH_3$ | 2-$FC_6H_4$ | — | 216-218/i-PrOH | 44 |
| 1T | $CH_3$ | 4-$CNC_6H_4$ | — | 211-213/EtOAc | 7 |
| 1U | $CH_3$ | $C_6H_5$ | 4-$CH_3$ | 176-179/EtOAc | 65 |
| 1V | $CH_3$ | 4-$C_2H_5C_6H_4$ | — | 199-201/EtOAc | 70 |
| 1W | $CH_3$ | 3-$NO_2C_6H_4$ | — | 218-221/DMF-$H_2O$ | 20 |
| 1X | $CH_3$ | 4-$CH_3C_6H_4$ | — | 207-209/EtOH | 60 |
| 1Y | $CH_3$ | 3-$CH_3OC_6H_4$ | — | 163-164/EtOAc | 63 |
| 1Z | H | 4-$CH_3OC_6H_4$ | — | | 80(b) |
| 1AA | $C_6H_5$ | 4-$CH_3OC_6H_4$ | — | | 25 |
| 1AB | H | $C_6H_5$ | 5-$CH_3O$ | | 46 |
| 1AC | $CH_3$ | 4-$CH_3OC_6H_4$ | 6-$CH_3O$ | | 53 |
| 1AD | $CH_3$ | 4-$NO_2C_6H_4$ | 6-$CH_3O$ | | 73 |
| 1AE | $CH_3$ | $C_6H_5$ | — | 185-186/MeOH | 64 |
| 1AF | H | $C_6H_5$ | — | 241-242/MeOH | 38 |
| 1AG | $CH_3$ | 4-$ClC_6H_4$ | — | 183-185/MeOH | 34 |
| 1AH | $CH_3$ | 4-$CH_3OC_6H_4$ | 6-Cl | | 58 |
| 1AI | $CH_3$ | 4-$CH_3OC_6H_4$ | 6-$C_6H_5CH_2O$ | | 51 |
| 1AJ | $CH_3$ | 2,3-$OCH_2OC_6H_3$ | — | 239.5-240/$CH_3CN$ | 98 |
| 1AK | $CH_3$ | 2-$C_6H_5C_6H_4$ | — | 238-240/MeOH | 39 |
| 1AL | $CH_3$ | 4-$C_6H_5C_6H_4$ | — | 225-228 | 56 |
| 1AM | $CH_3$ | 1-naphthyl | — | 223-224/i-PrOH | 69 |
| 1AN | $CH_3$ | 2,3-$(CH_3O)_2C_6H_3$ | — | 185-187 | 87 |
| 1AO | $CH_3$ | 3,5-$(CH_3O)_2C_6H_3$ | — | 182-184 | 85 |
| 1AP | $CH(CH_3)_2$ | 4-$CH_3OC_6H_4$ | — | 176-178/EtOAc-ether | 44 |
| 1AQ | $CH(CH_3)_2$ | 4-$CH_3OC_6H_4$ | 5-F | 173-175 | 11 |
| 1AR | $CH_3$ | 2-$FC_6H_4$ | 5-F | 247-249/i-PrOH | 10 |
| 1AS | $CH_3$ | 4-$CH_3O$-1-naphthyl | — | 286-289/i-PrOH | 24 |
| 1AT | $CH_3$ | 4-$C_6H_5C_6H_4$ | 5-F | 234-235.5/EtOH | 36 |

TABLE A-continued

| Prepn. | R₂ | R₃ | R₄ | m.p./Solv. | Yield |
|---|---|---|---|---|---|
| 1AU | CH₃ | 4-CH₃OC₆H₄ | — | 200-203 | 97 |

(a)Product consisted of a mixture of the 5-fluoro and the 7-fluoro isomers.
(b)Two molar equivalents of the Grignard reagent used, thus resulting in acylation at both the 1- and 3- positions of indole derivative. The desired product was obtained by heating a mixture of the crude product in methanol and sodium hydroxide.

Preparation 1AV

A mixture of 50 g. (0.03 mole) of phenylmercaptoacetone and 76.8 g. (0.3 mole) of 3-benzyloxyphenylhydrazine in 750 ml. of ethanol was heated on a steam bath for six hours and then stirred at room temperature for about twelve hours. The solid which separated was collected, washed with water and the filtrate set aside. The solid was dissolved in methylene dichloride, the organic solution was washed with water, then with dilute hydrochloric acid, dried over magnesium sulfate, filtered and taken to dryness to yield a first crop of crude product which was stirred with ether for about forty-eight hours and then filtered and dried to give 56 g. of product. The original filtrate, previously set aside, was mixed with methylene dichloride, and the organic layer was washed with water, then with dilute hydrochloric acid, dried over magnesium sulfate, filtered and concentrated to dryness to give 40 g. of additional product which was recrystallized from diethyl ether/methylene dichloride to give 29.7 g. of product (combined yield 71.7 g., 69%) of 2-methyl-3-phenylmercapto-6-benzyloxyindole, m.p. 146°-148° C.

A mixture of 25 g. (0.072 mole) of the latter with 50 teaspoons of a Raney nickel/ethanol suspension in 1 liter of ethanol was heated under reflux for three hours, stirred at ambient temperature for about twelve hours, then refluxed for an additional three hours and the catalyst removed by filtration. The filtrate was taken to dryness in vacuo to give an oil which was passed through a pad of Florisil and eluted with ethyl acetate. Evaporation of the solution to dryness afforded 5.2 g. (26%) of 6-hydroxy-2-methylindole.

A mixture of 5 g. (0.034 mole) of the latter, 5.9 ml (0.051 mole) of benzyl chloride and 13.8 g. (0.1 mole) of potassium carbonate in 200 ml of DMF was stirred at room temperature for two hours, then heated on a steam bath for two hours and the mixture poured into ice/water. The solid which separated was collected, dissolved in ethyl acetate, and the organic solution was washed with water, then with brine, dried over magnesium sulfate, filtered and taken to dryness to give 2.5 g. of 6-benzyloxy-2-methylindole, m.p. 90°-93° C., used as the starting material for the preparation of the compound of Preparation 1AI in Table 1 above.

Preparation 2

To a solution of 20 g. (0.071 mole) of 2-methyl-3-(4-methylmercaptobenzoyl)indole (Preparation 1D) in 400 ml. of chloroform was added, dropwise with stirring, a solution of 16.7 g.(0.081 mole) of 3-chloroperbenzoic acid (80%) in 170 ml. of chloroform while cooling the mixture in an ice/methanol bath. When addition was complete, the solution was stirred at room temperature for approximately twelve hours and then washed three times with saturated sodium bicarbonate solution and dried over magnesium sulfate. The mixture was filtered, the filtrate was concentrated to near dryness, and the solid which separated was collected and recrystallized from ethyl acetate to give 14.5 g. (69%) of 2-methyl-3-(4-methylsulfinylbenzoyl)indole.

Preparation 3

2-Methyl-3-(4-nitrobenzoyl)indole (Preparation 1E) (11.2 g., 0.04 mole) dissolved in a solution of 100 ml. of glacial acetic acid and 200 ml. of ethyl acetate was reduced with hydrogen over 0.6 g. of platinum oxide catalyst in a Parr shaker, and when reduction was complete, in about two and a half hours, the catalyst was removed by filtration and the solvent taken off in vacuo to leave 11.4 g. of crude product, which was recrystallized from ethanol to give 4.5 g. (45%) of 2-methyl-3-(4-aminobenzoyl)indole, m.p. 220°-223° C.

B. The Compounds of Formula III (a) By Alkylation of the Compounds of Formula IV Preparation 4A To a stirred suspension of 229.5 g. (1.22 moles) of N-(2-chloroethyl)morpholine hydrochloride in 300 ml. of DMSO at ambient temperature was added 200 g. (3.03 moles) of 85% potassium hydroxide pellets, and the suspension was stirred for five minutes and then treated dropwise at ambient temperature with a solution of 133.7 g. (1.0 mole) of 2-methylindole in 140 ml. of DMSO. The temperature of the reaction mixture gradually rose during the addition of the 2-methylindole as well as on stirring after addition was complete. When the temperature reached 78° C., the mixture was cooled in a water bath until the temperature subsided to 75° C., and the mixture was stirred for a total of three and a half hours while the temperature subsided to ambient. The mixture was then diluted with 1 liter of water and extracted with toluene. The extracts were washed with water, dried over magnesium sulfate and taken to dryness in vacuo, and the residual dark oil was crystallized from heptane to give 224 g. (92%) of 2-methyl-1-[2-(4-morpholinyl)ethyl]-1H-indole, m.p. 63°-65° C.

Preparation 4B

Following a procedure similar to that described above in Preparation 4A, 20.0g. (0.134 mole) of 5-fluoro-2-methylindole were reacted with 24.1 g. (0.147 mole) of 4-(3-chloropropyl)morpholine in 46 ml. of dry DMF in the presence of 8.0 g. (0.201 mole) of a 60% mineral oil dispersion of sodium hydride. The product was isolated in the form of its maleate salt to give 30.0 g. (81%) of 5-fluoro-2-methyl-1-[3-(4-morpholinyl)propyl]-1H-indole maleate, m.p. 165°-167° C.

Preparation 4C

Following a procedure similar to that described in Preparation 4A, 50 g. (0.43 mole) of indole were reacted with 159 g. (0.85 mole) of 4-(2-chloroethyl)morpholine in 850 ml. of dry DMF in the presence of 209 g. (0.50 mole) of a 60% mineral oil dispersion of sodium hydride. The product was isolated in the form of the free base to give 45.6 g. (46%) of 1-[2-(4-morpholinyl)ethyl]-1H-indole.

Preparation 4D

To a stirred suspension of 322 g. (0.81 mole) of a 60% mineral oil dispersion of sodium hydride in 250 ml. of dry DMF was added dropwise a solution of 100 g. (0.67 mole) of 5-fluoro-2-methylindole in 300 ml. of dry DMF. The mixture was stirred at ambient temperature for thirty minutes and then treated dropwise with cooling with a solution of 121.5 g. (0.67 mole) of ethyl α- bromopropionate. Workup of the reaction mixture, after quenching with water and extraction of the product with ethyl acetate, afforded ethyl α-(5-fluoro-2-methyl-1-indolyl)propionate.

The latter was reduced with 525 ml. of a 1M solution of diisobutyl aluminum in 1150 ml. of toluene to give 130 g. (94%) of 5-fluoro-2-methyl-1-(1-methyl-2-hydroxyethyl)-1H-indole.

The latter, on reaction with 144 g. (0.76 mole) of p-toluenesulfonyl chloride in 350 ml. of pyridine using the procedure described in Preparation 7A afforded 65 g. (20%) of 5-fluoro-2-methyl-1-[1-methyl-2-(p-toluenesulfonyloxy)ethyl]-1H-indole, m.p. 136°–140° C.

(b) Via the Amides of Formula V

Preparation 5A

Following a procedure similar to that described in Preparation 4 above, 32.8 g. (0.25 mole) of 2-methylindole in 160 ml. of dry DMF was reacted with 13.4 g. (0.28 mole) of a 50% mineral oil dispersion of sodium hydride in 200 ml. of dry DMF, and the resulting sodium salt was then reacted with 62 g. (0.28 mole) of 4-(α-bromopropionyl)morpholine in 160 ml. of DMF to give 55.3 g. (59%) of 4-[α-(2-methyl-1H-indol-1-yl)propionyl]morpholine.

The latter (130 g., 0.48 mole), dissolved in 900 ml. of THF, was added to 80 ml. (0.80 mole) of a solution of boron methyl sulfide complex in THF under nitrogen while cooling in an ice bath. When addition was complete, the mixture was stirred for eighteen hours at room temperature, heated under reflux for four hours, quenched by addition of about 1 liter of methanol, boiled for about fifteen minutes, concentrated essentially to dryness and then diluted with aqueous 6N hydrochloric acid. The mixture was extracted with methylene dichloride, and the raffinate was basified with 35% sodium hydroxide and extracted with ethyl acetate. The combined organic extracts were washed with brine, dried and concentrated to dryness to give 42.6 g. (34%) of 2-methyl-1-[1-methyl-2-4-morpholinyl)ethyl]-1H-indole as an oil. A portion of the latter was reacted with methanesulfonic acid to give the monomethanesulfonate as the 4:1 hydrate, m.p. 154°–157° C.

Preparation 5B

Following a procedure similar to that described in Preparation 5A above, 29.29 g. (0.25 mole) of indole in 200 ml. of dry DMF was reacted with 13.4 g. (0.28 mole) of a 50% mineral oil dispersion of sodium hydride in 200 ml. of dry DMF and the resulting sodium salt reacted with 62.0 g. (0.28 mole) of 4-(α-bromopropionyl)morpholine in 200 ml. of dry DMF and the product recrystallized from isopropanol to give 13.7 g. (21%) of 4-[α-(1H-indol-1-yl)propionyl]morpholine, m.p. 92°–94° C. The latter (20 g., 0.078 mole) in 300 ml. of diethyl ether was reduced with 3.12 g. (0.078) mole of lithium aluminum hydride in 100 ml. of diethyl ether to give 17 g. (90%) of 1-[1-methyl-2-(4-morpholinyl)ethyl]-1H-indole, m.p. 35°–37° C.

Preparation 5C

Following a procedure similar to that described in Preparation 5B, 83 g. (0.63 mole) of 2-methylindole was reacted with 30 g. (0.75 mole) of a 60% mineral oil dispersion of sodium hydride, and the resulting sodium salt was reacted with a molar equivalent amount of 4-(α-bromobutyryl)morpholine in 100 ml. of DMF. The crude product thus obtained was reduced with 25 g. (0.66 mole) of lithium aluminum hydride in 500 ml. of THF. The product was isolated in the form of the hydrochloride to give 53.4 g. (27%) of 2-methyl-1-[1-ethyl-2-(4-morpholinyl)ethyl]-1H-indole hydrochloride, m.p. 159°–162° C. (from ethyl acetateether).

Preparation 6

To a solution of 23 g. (0.1 mole) of 1-[2-(4-morpholinyl)ethyl]-1H-indole (Preparation 4C) in 120 ml. of THF was added 60 ml. of 2.1M butyl lithium in hexane while maintaining the temperature at 0° C. The mixture was allowed to warm up to room temperature and was then treated with 18 ml. of hexamethylphosphoramide followed by 10 ml. of ethyl iodide while maintaining the temperature at 0° C. The mixture was then quenched with ice, extracted with ether, and the combined organic extracts were washed first with water, then with brine, dried over magnesium sulfate, taken to dryness and chromatographed on silica gel, eluting with 40:50 ethyl acetate:hexane. Four fractions were obtained which, on evaporation to dryness, afforded 4.0 g. of a yellow oil from the first fraction and 9.6 g., 3.6 g. and 4.2 g. of solid material in the next three fractions. These fractions were recrystallized from hexane to give 8.3 g. (32%) of 2-ethyl-1-[2-(4-morpholinyl)ethyl]-1H-indole, m.p. 59°–60.5° C.

C. The Compounds of Formula VI

Preparation 7A

To a suspension of 50 g. (0.19 mole) of 2-methyl-3-(4-methoxybenzoyl)indole (Preparation 1AU) in 400 ml. of THF was added, over a one and a half hour period, 74.25 ml. (0.19 mole) of a 2.6M solution of n-butyl lithium in hexane. The reaction mixture was stirred for one hour at 0° C., at room temperature for forty-five minutes, recooled to 0° C. and treated dropwise, over a thirty minute period, with a solution of 93.7 ml. (0.19 mole) of a 2.06 M solution of ethylene oxide in THF. The reaction mixture was gradually allowed to warm to room temperature and then treated with 200 ml. of a saturated ammonium chloride solution. The solvent was removed in vacuo, the residual solid was filtered, washed with water and extracted with boiling ether, and the ether extracts were taken to dryness to give 23 g. (39%) of 2-methyl-3-(4-methoxybenzoyl)-1-(2-hydroxyethyl)-1H-indole, m.p. 75°–78° C.

A solution of 10 g. (0.032 mole) of the latter and 6.48 g. (0.034 mole) of p-toluenesulfonyl chloride in 100 ml. of pyridine was stirred at room temperature for about twelve hours and the reaction mixture diluted with ethyl acetate and washed with water. The organic layer was separated, dried over magnesium sulfate, filtered and concentrated to dryness to give a brown gum. The latter was dissolved in methylene dichloride and the solution chromatographed on a short column of Florisil to give 7.8 g. (52%) of 2-methyl-3-(4-methoxybenzoyl)-1-(2-p-toluenesulfonyloxyethyl)-1H-indole, m.p. 62°–65° C.

Preparation 7B

Following a procedure similar to that described in Preparation 7A above, 9.75 g. (0.0375 mole) of 2-methyl-3-(4-cyanobenzoyl)indole (Preparation 1T) in 125 ml. of THF was treated with 16.65 ml. (0.04 mole) of a 2.4M solution of n-butyl lithium in hexane followed by 11.4 ml. of a 3.5M solution of ethylene oxide in THF to give 2-methyl-3-(4-cyanobenzoyl)-1-(2-hydroxyethyl)-1H-indole. Reaction of 30.4 g. (0.1 mole) of the latter with 21.0 g. (0.11 mole) of p-toluenesulfonyl chloride in 50 ml. of methylene dichloride in the presence of 50 ml. of 35% sodium hydroxide and 0.91 g. (0.004 mole) of benzyl trimethylammonium chloride afforded 38.3 g. (84%) of 2-methyl-3-(4-cyanobenzoyl)-1-(2-p-toluenesulfonyloxyethyl)-1H-indole, m.p. 165°–167° C.

Preparation 7C

Following a procedure similar to that described in Preparation 7A above, 20 g. (0.1 mole) of 2-methyl-3-(4-ethylbenzoyl)indole (Preparation 1V) in 200 ml. of THF was treated with 51 ml. (0.11 mole) of a 2.15 M solution of n-butyl lithium in hexane followed by 6.16 g. (0.13 mole) of ethylene oxide to give 18 g. (73%) of 2-methyl-3-(4-ethylbenzoyl)-1-(2-hydroxyethyl)-1H-indole. Reaction of the latter (0.058 mole) with 14.32 g. (0.075 mole) of p-toluenesulfonyl chloride in 400 ml. of methylene dichloride in the presence of 50 ml. of 35% sodium hydroxide and 1.6 g. (0.0076 mole) of benzyl trimethylammonium chloride afforded 27 g. (95%) of 2-methyl-3-(4-ethylbenzoyl)-1-(2-p-toluenesulfonyloxyethyl)-1H-indole as a red oil.

Preparation 7D A solution of 5.0 g. (0.068 mole) of 2-methyl-5fluoro-3-(4-methoxybenzoyl)indole (Preparation 1F) in 100 ml. of dry DMF was cooled in an ice bath at 0° C and then treated with 18.17 g. (0.09 mole) of 1,3-dibromopropane. The solution was stirred for a few minutes at 0° C, then treated portionwise with 1.08 g. (0.027 mole) of a 60% mineral oil dispersion of sodium hydride, stirred for about fifteen minutes in an ice bath, then for an additional twelve hours at ambient temperature, treated with a small amount of water and taken to dryness in vacuo. The residue was partitioned between water and methylene dichloride, the organic layer was separated, washed first with water, then with brine and then dried and taken to dryness. Crystallization of the residue from ethanol afforded 4 g. (55%) of 1-(3-bromopropyl)-5-fluoro-2-methyl-3-(4-methoxybenzoyl)-1H-indole, m.p. 133°–135° C.

Preparation 7E

Following a procedure similar to that described in Preparation 7D above, 60 g. (0.23 mole) of 2-methyl-3-(4-methoxybenzoyl)indole (Preparation 1AU) was reacted with 244.1 g. (1.13 mole) of 1,4-dibromobutane in 200 ml. of DMF in the presence of 13.8 g. (0.34 mole) of a 60% mineral oil dispersion of sodium hydride, and the product recrystallized from ethyl acetate/hexane to give 5.0 g. of 1-(4-bromobutyl)-2-methyl-3-(4-methoxybenzoyl)-1H-indole, m.p. 83°–86° C.

Preparation 7F

Following a procedure similar to that described in Preparation 7D above, 35 g. (0.122 mole) of 2-methyl-3-(1naphthylcarbonyl)indole (Preparation 1AM) was reacted with 124 g. (0.614 mole) of 1,3-dibromopropane in 700 ml of DMF in the presence of 7.5 g. (0.188 mole) of a 60% mineral oil dispersion of sodium hydride, and the product purified by chromatography on Kieselgel 60 in 50% ethyl acetate/hexane. There was thus obtained 18.38 g. (37%) of 1-(3-bromopropyl)-2-methyl-3-(1-naphthylcarbonyl)-1H-indole, m.p. 115°–116° C.

Preparation 7G

Following a procedure similar to that described in Preparation 7D above, 73.86 g. (0.3 mole) of 2-methyl-3-(4-methoxybenzoyl)indole (Preparation 1AU) was reacted with 302.33 g. (1.5 moles) of 1,3-dibromopropane in 250 ml. of DMF in the presence of 17.97 g. (0.45 mole) of a 60% mineral oil dispersion of sodium hydride. There was thus obtained 1-(3-bromopropyl)-2-methyl-3-(4-methoxybenzoyl)-1H-indole.

Preparation 7H

Following a procedure similar to that described in Preparation 7D above, 15.0 g. (0.053 mole) of 5-fluoro-2-methyl-3-(4-methoxybenzoyl)indole (Preparation 1F) was reacted with 9.18 g. (0.058 mole) of 1-bromo-3-chloropropane in 232 ml. of DMF in the presence of 3.2 g. (0.0795 mole) of a 60% mineral oil dispersion of sodium hydride. There was thus obtained 15.3 g. (80%) of 1-(3-chloropropyl)-5-fluoro-2-methyl-3-(4-methoxybenzoyl)-1H-indole.

Preparation 7I

Following a procedure similar to that described in Preparation 7A above, 24.8 g. (0.087 mole) of 2-methyl-3(1-naphthylcarbonyl)indole (Preparation 1AM) in 300 ml. of THF was treated with 35 ml. (0.09 mole) of a 2.6M solution of n-butyl lithium in hexane followed by 56 ml. of a 2.6M solution of ethylene oxide in THF to give 21.3 g. (74%) of 2-methyl-3-(1-naphthylcarbonyl)-1-(2-hydroxyethyl)-1H-indole. Reaction of the latter (0.065 mole) with 18.5 g. (0.097 mole) of p-toluenesulfonyl chloride in 400 ml. of methylene dichloride in the presence of 340 ml. of 35% sodium hydroxide and 0.6 g. (0.0026 mole) of benzyl trimethylammonium chloride afforded 20.1 g. (64%) of 2-methyl-3-(1-naphthylcarbonyl)-1-(2-p-toluenesulfonyloxyethyl)-1H-indole as a viscous oil.

Preparation 8

A solution of 42 g. (0.116 mole) of 5-fluoro-2-methyl-1-[1-methyl-2-(p-toluenesulfonyloxy)ethyl]-1H-indole (Preparation 4D) and 50 ml. of morpholine in 400 ml. of DMF was heated on a steam bath for seventy-two hours, poured into water and the mixture extracted with ethyl acetate. The combined organic extracts were dried and taken to dryness to give 20 g. of crude product which was purified by HPLC, eluting the product with 2:1 hexane:ethyl acetate. There was thus obtained 10.4 g. (32%) of 5-fluoro-2-methyl-1-[1-methyl-2-(4-morpholinyl)ethyl]-1H-indole as the first, third and fourth through the seventh fractions.

The second fraction, on conversion to the hydrochloride salt and recrystallization from methanol-ether, afforded 1.0 g. of 5-fluoro-2-methyl-1-[1-methyl-2-(dimethylamino)ethyl]-1H-indole hydrochloride, m.p. 208.5°–211.5° C., produced by amination of the tosylate by the DMF used as a solvent.

It is contemplated that, by replacing the morpholine in the above-described procedure with dimethylamine, the dimethylamino species can be obtained as the major product.

Preparation 9A

Following a procedure similar to that described in Preparation 5A above, 24.0 g. (0.071 mole) of 5-fluoro-2-methyl-3-(4-methoxybenzoyl)indole (Preparation 1F) in 200 ml. of dry DMF was reacted with 35.2 g. (0.35 mole) of epichlorohydrin in the presence of 3.1 g. (0.078 mole) of a 60% mineral oil dispersion of sodium hydride in 100 ml. of DMF. The product was recrystallized from ethyl acetatehexane to give 10.6 g. (44%) of 5-fluoro-2-methyl-3-(4-methoxybenzoyl)-1-[1-(2,3-epoxy)propyl]-1H-indole as a yellow solid.

Preparation 9B

Following a procedure similar to that described in Preparation 9A above, 100 g. (0.377 mole) of 2-methyl-3-(4-methoxybenzoyl)indole (Preparation 1AU) in 1500 ml. of DMF was reacted with 174.6 g. (1.89 moles) of epichlorohydrin in the presence of 19.92 g. (0.42 mole) of a 50% mineral oil dispersion of sodium hydride in 500 ml. of DMF. There was thus obtained 2-methyl-3-(4-methoxybenzoyl)-1-[1-(2,3-epoxy)propyl]-1H-indole.

Preparation 9C

Following a procedure similar to that described in Preparation 9A above, 28.7 g. (0.1 mole) of 2-methyl-3-(1-naphthylcarbonyl)indole (Preparation 1AM) in 165 ml. of DMSO was reacted with 27.39 g. (0.2 mole) of epibromohydrin in the presence of 6.6 g. (0.1 mole) of powdered potassium hydroxide and the product purified by chromatography on silica gel, eluting with ethyl acetate-hexane. There was thus obtained 32.3 g. (95%) of 2-methyl-3-(1-naphthyl-carbonyl)-1-[1-(2,3-epoxy)propyl]-1H-indole.

PREPARATION OF THE FINAL PRODUCTS OF FORMULA I

A. From the Compounds of Formula II

Example 1A

Following a procedure similar to that described in Preparation 4 above, 25 g. (0.10 mole) of 3-(4-methoxybenzoyl)indole (Preparation 1Z) in 100 ml. of DMF was reacted with 5.76 g. (0.12 mole) of a 50% dispersion of sodium hydride in mineral oil in 120 ml. of DMF, and the resulting sodium salt was reacted with 0.14 mole of 4-(2-chloroethyl)morpholine (freed from 26.06 g. of the corresponding hydrochloride) in 120 ml. of DMF to give 42 g. of the crude product as an oil which, on trituration with ethyl acetate/diethyl ether/hexane, gave a yellow crystalline solid which was converted to the methanesulfonate salt to afford 9.5 g. (20%) of 3-4-methoxybenzoyl)-1-[2-(4-morpholinyl)ethyl]-1H-indole methanesulfonate monohydrate, m.p. 110°–112° C.

Examples 1B–1CR

Following a procedure similar to that described in Example 1A above, the following species of formula I in Table 1 were prepared by reaction of a 2-$R_2$-3-$R_3$-carbonyl-1H-indole of formula II with an appropriate halo alkylamine or tosyloxyalkylamine. The acid-acceptor and reaction solvent used in the reactions are given in the column headed "Cat./Solv.". Here and elsewhere in the tables, the form in which the product was isolated, either as the free base or as an acid-addition salt, is given in columns headed "Base/Salt", and the abbreviations "Morph.", "Pip." and "Pyr." in the columns headed N=B represent the 4-morpholinyl, 1-piperidinyl and 1-pyrrolidinyl groups, respectively. In Table 1, unless noted otherwise, an appropriate chloroalkylamine was used as the alkylating agent. Here and elsewhere in the specification and the claims, the alkylene groups, Alk, are depicted as they would appear with the 1-indolyl moiety attached to the carbon atom at the left end of the alkylene chain and with the amine group, N=B, attached to the carbon at the right end of the chain.

TABLE 1

| Example | R₂ | R₃ | R₄ | Alk | N=B | Cat./Solv. | Base/Salt | m.p./Solv. | Yield |
|---|---|---|---|---|---|---|---|---|---|
| IB | CH₃ | 4-CH₃OC₆H₄ | — | (CH₂)₂ | Morph. | K₂CO₃/DMF | Base(c) | 104-105/EtOAc-hexane | 37 |
| IC | CH₃ | 2-furyl | — | (CH₂)₂ | Morph. | K₂CO₃/DMF | HCl.H₂O | 190-192/ether | 35 |
| ID | CH₃ | 4-CH₃SC₆H₄ | — | (CH₂)₂ | Morph. | K₂CO₃/DMF | Base | 125-126/EtOAc-hexane | 36 |
| IE | CH₃ | 4-CH₃OC₆H₄ | 7-CH₃ | (CH₂)₂ | Morph. | NaH/DMF | Base | 149-151/i-PrOH | 83 |
| IF | CH₃ | 4-CH₃SOC₆H₄ | — | (CH₂)₂ | Morph. | K₂CO₃/DMF | HH₂O | 103-105/EtOAc-hexane | 68 |
| IG | CH₃ | 4-CH₃OC₆H₄ | — | (CH₂)₂ | Morph. | NaH/DMF | HCl | 198-200/MeOH-ether | 59 |
| IH | CH₃ | 4-CH₃OC₆H₄ | 5-F | (CH₂)₂ | Morph. | NaH/DMF | HCl | 248-249/MeOH-ether | 53 |
| II | CH₃ | 4-CH₃OC₆H₄ | — | (CH₂)₃ | Morph. | NaH/DMF | HCl | 222-224/i-PrOH-ether | 50 |
| IJ | CH₃ | 4-CH₃OC₆H₄ | 5-F | (CH₂)₂ | Morph. | NaH/DMF | HCl | 202-203/i-PrOH-ether | 53 |
| IK | CH₃ | 4-CH₃OC₆H₄ | — | (CH₂)₂ | Pyr. | NaH/DMF | HCl | 233-235/McOH-ether | 41 |
| IL | CH₃ | 4-CH₃OC₆H₄ | — | (CH₂)₂ | Pip. | NaH/DMF | HCl | 228-230/MeOH-ether | 31 |
| IM | CH₃ | 4-CH₃OC₆H₄ | 7-F | (CH₂)₂ | Morph. | MaH/DMF | CH₃SO₃H | 120-121/i-PrOH | 23 |
| IN | CH₃ | 4-CH₃OC₆H₄ | 7-CH₃O | (CH₂)₂ | Morph. | NaH/DMF | HCl | 203-204 | 25 |
| I-O | CH₃ | 4-CH₃OC₆H₄ | 6-Cl | (CH₂)₂ | Morph. | NaH/DMF | Base | 138-139/i-PrOH | 3 |
| IP | CH₃ | 4-CH₃OC₆H₄ | 4-/6-F(d) | (CH₂)₂ | Morph. | NaH/DMF | HCl | 127-128/DMF | 39 |
| IQ | CH₃ | 4-FC₆H₄ | — | (CH₂)₂ | Morph. | K₂CO₃/DMF | CH₃SO₃H | 209-211/i-PrOH | 70 |
| IR | CH₃ | 3,4-OCH₂OC₆H₃ | — | (CH₂)₂ | Morph. | K₂CO₃/DMF | CH₃SO₃H | 142-145/i-PrOH | 33 |
| IS | CH₃ | 2-benzo[b]furyl | — | (CH₂)₂ | Morph. | K₂CO₃/DMF | CH₃SO₃H | 194-198/EtOH | 60 |
| IT | CH₃ | 3-benzo[b]thienyl | — | (CH₂)₂ | Norph. | K₂CO₃/DMF | CH₃SO₃H.H₂O | 155-158/EtOH | 55 |
| IU | CH₃ | 2-CH₃OC₆H₄ | — | (CH₂)₂ | Morph. | K₂CO₃/DMF | CH₃SO₃H | 199-214/i-PrOH | 65 |
| IV | CH₃ | 3-F-4-CH₃OC₆H₄ | — | (CH₂)₂ | Morph. | K₂CO₃/DMF | CH₃SO₃H(e) | 130-135/i-PrOH | 63 |
| IW | CH₃ | 2-naphthyl | — | (CH₂)₂ | Morph. | K₂CO₃/DMF | CH₃SO₃H | 195-198/i-PrOH | 35 |
| IX | H | 4-CH₃OC₆H₄ | 5-CH₃ | (CH₂)₂ | Morph. | K₂CO₃/DMF | CH₃SO₃H | 150-151/i-PrOH | 45 |
| IY | CH₃ | 3-FC₆H₄ | — | (CH₂)₂ | Morph. | K₂CO₃/DMF | Base | 130-131/i-PrOH | 77 |
| IZ | CH₃ | 2-FC₆H₄ | — | (CH₂)₂ | Morph. | K₂CO₃/DMF | Base | 112-114/i-PrOH | 65 |
| IAA | CH₃ | 4-CNC₆H₄ | 4-CH₃ | (CH₂)₂ | Morph. | K₂CO₃/DMF | CH₃SO₃H | 198-200/i-PrOH | 29 |
| IAB | CH₃ | C₆H₅ | — | (CH₂)₃ | Morph. | K₂CO₃/DMF | Base | 116-117.5/EtOAc | 46 |
| IAC | CH₃ | 4-C₂H₅C₆H₄ | — | (CH₂)₂ | Morph. | K₂CO₃/DMF | Base | 124-126/EtOAc | 70 |
| IAD | CH₃ | 3-NO₂C₆H₄ | — | (CH₂)₂ | Morph. | K₂CO₃/DMF | Base | 141-143/EtOAc | 67 |
| IAE | CH₃ | 4-CH₃SC₆H₄ | — | (CH₂)₂ | Morph. | K₂CO₃/DMF | Base | 120.5-121.5/EtOAc | 60 |
| IAF | CH₃ | 4-CNC₆H₄ | — | (CH₂)₂ | Morph. | K₂CO₃/DMF | Base | 156.5-158.5/EtOAc | 89 |
| IAG | CH₃ | 4-C₆H₅CH₂OC₆H₄ | — | (CH₂)₂ | Morph. | K₂CO₃/DMF | Base | 140-141/EtOH | 69 |
| IAH | CH₃ | 3-CH₃OC₆H₄ | — | (CH₂)₂ | Morph. | K₂CO₃/DMF | Base | 130-131/EtOAc | 84 |
| IAI | CH₃ | 3,4-(CH₃O)₂C₆H₃ | — | (CH₂)₂ | Morph. | K₂CO₃/DMF | Base | 230-233/i-PrOH | 64 |
| IAJ | C₆H₅ | 4-CH₃OC₆H₄ | — | (CH₂)₂ | Morph. | NaH/DMF | HCl | 90-92 | 29 |
| IAK | H | C₆H₅ | 5-CH₃O | (CH₂)₂ | Morph. | NaH/DMF | Base | 98-101 | 55 |
| IAL | CH₃ | C₆H₅ | 5-CH₃O | (CH₂)₃ | Morph. | NaH/DMF | Base | 88-90 | 50 |
| IAM | CH₃ | 4-CH₃OC₆H₄ | 6-CH₃O | (CH₂)₂ | Morph. | K₂CO₃/DMF | Base | 222-224/EtOAc-MDC-ether | 63 |
| IAN | CH₃ | 4-NO₂C₆H₄ | 6-CH₃O | (CH₂)₂ | Morph. | K₂CO₃/DMF | HCl | 126-128 | 46 |
| IAO | CH₃ | C₆H₅ | — | (CH₂)₂ | Morph. | NaH/DMF | HCl | 111-112/EtOAc-hexane | 78 |
| IAP | H | C₆H₅ | — | (CH₂)₂ | Morph. | NaH/DMF | Base | 101-103/EtOAc-hexane | 69 |
| IAQ | CH₃ | 4-ClC₆H₄ | — | (CH₂)₂ | Morph. | NaH/DMF | Base | 148-150/EtOAc | 54 |
| IAR | H | 4-ClC₆H₄ | — | (CH₂)₂ | Morph. | NaH/DMF | Base | 136-138/EtOAc-hexane | 60 |
| IAS | CH₃ | 3,4-Cl₂C₆H₃ | — | (CH₂)₂ | Morph. | K₂CO₃/DMF | HCl | 128-130/EtOAc-hexane | 44 |
| IAT | H | 2-thienyl | — | (CH₂)₂ | Morph. | K₂CO₃/DMF | HCl | 230-240/MeOH—H₂O-ether | 66 |
| IAU | CH₃ | 4-ClC₆H₄ | 6-CH₃O | (CH₂)₂ | Morph. | K₂CO₃/DMF | HCl | 275-285/EtOH—H₂O | 52 |
| IAV | CH₃ | 2-thienyl | 6-CH₃O | (CH₂)₂ | Morph. | K₂CO₃/DMF | HCl | 224-228/EtOAc-hexane | 100 |
| IAW | CH₃ | C₆H₅ | — | CHCH₃CH₂ | Morph. | K₂CO₃/DMF | Base | 137-139/EtOAc-hexane | 1.3 |

TABLE 1-continued

| Example | R$_2$ | R$_3$ | R$_4$ | Alk | N=B | Cat./Solv. | Base/Salt | m.p./Solv. | Yield |
|---|---|---|---|---|---|---|---|---|---|
| 1AX(f) | CH$_3$ | C$_6$H$_5$ | — | CH$_2$CHCH$_3$ | Morph. | K$_2$CO$_3$/DMF | Base | 108-110/EtOAc-hexane | 48 |
| 1AY(g) | H | C$_6$H$_5$ | — | CHCH$_3$CH$_2$ | Morph. | K$_2$CO$_3$/DMF | Base | 123-125/EtOAc-hexane | 7 |
| 1AZ(g) | H | C$_6$H$_5$ | — | CH$_2$CHCH$_3$ | Morph. | K$_2$CO$_3$/DMF | Base | 97-100/EtOAc-hexane | 48 |
| 1BA | H | C$_6$H$_5$ | 7-CH$_3$ | (CH$_2$)$_2$ | Morph. | K$_2$CO$_3$/DMF | Base | 131-133/EtOAc-hexane | 80 |
| 1BB | CH$_3$ | 1-naphthyl | — | (CH$_2$)$_2$ | Morph. | K$_2$CO$_3$/DMF | Base | 122-124/i-PrOH | 40 |
| 1BC | CH$_3$ | 4-CNC$_6$H$_4$ | — | (CH$_2$)$_2$ | Pyr. | NaH/DMF | Base | 138-139/i-PrOH | 22 |
| 1BD | CH$_3$ | 4-CH$_3$OC$_6$H$_4$ | — | (CH$_2$)$_2$ | N(CH$_3$)$_2$ | NaH/DMF | HCl | 237-240/MeOH | 56 |
| 1BE | CH$_3$ | 4-CH$_3$OC$_6$H$_4$ | — | (CH$_2$)$_2$ | N(C$_2$H$_5$)$_2$ | NaH/DMF | HCl | 209-211/EtOAc-ether | 62 |
| 1BF | CH$_3$ | 4-CH$_3$OC$_6$H$_4$ | — | (CH$_2$)$_2$ | Morph. | NaH/DMF | Base | 127-128/DMF | 38 |
| 1BG | CH$_3$ | 4-PrOC$_6$H$_4$ | — | (CH$_2$)$_2$ | Morph. | K$_2$CO$_3$/DMF | Base.¼H$_2$O | 104.5-105.5/EtOAc | 39 |
| 1BH | CH$_3$ | 4-EtOC$_6$H$_4$ | — | (CH$_2$)$_2$ | Morph. | K$_2$CO$_3$/DMF | Base | 93-97/i-PrOH | 68 |
| 1BI | CH$_3$ | 4-CH$_3$(O-1-naphthyl | — | (CH$_2$)$_2$ | Morph. | K$_2$CO$_3$/DMF | Base | 145-147/i-PrOH | 26 |
| 1BJ | CH$_3$ | 6-CH$_3$(O-2-naphthyl | — | (CH$_2$)$_2$ | Morph. | K$_2$CO$_3$/DMF | CH$_3$SO$_3$H.0.4 i-PrOH | 159-160/EtOAc | 4,9 |
| 1BK | CH$_3$ | 4-CH$_3$OC$_6$H$_4$ | 6-C$_6$H$_5$CH$_2$O | (CH$_2$)$_2$ | Morph. | K$_2$CO$_3$/DMF | Base | EtOAc | 46 |
| 1BL | CH$_3$ | 4-CNC$_6$H$_4$ | 5-F | (CH$_2$)$_2$ | Morph. | NaH/DMF | Base | 225-227/MeOH-ether | 35 |
| 1BM | H | 4-CH$_3$OC$_6$H$_4$ | 5-F | (CH$_2$)$_2$ | Morph. | NaH/DMF | HCl.½H$_2$O | 172-174/i-PrOH | 67 |
| 1BN | CH$_3$ | 4-CH$_3$OC$_6$H$_4$ | 5-F | (CH$_2$)$_2$ | Pip. | NaH/DMF | HCl | 199-201/MeOH-ether | 40 |
| 1BO | CH$_3$ | 4-CH$_3$OC$_6$H$_4$ | 5-F | (CH$_2$)$_2$ | Morph. | NaH/DMF | HCl | 244-245/MeOH-ether | 81 |
| 1BP | CH$_3$ | C$_6$H$_5$ | — | (CH$_2$)$_3$ | N(C$_2$H$_5$)$_2$ | NaH/DMF | HCl | 124-126/MeOH-ether | 52 |
| 1BQ | CH$_3$ | 4-CH$_3$OC$_6$H$_4$ | 5-Cl | (CH$_2$)$_3$ | Morph. | NaH/DMF | HCl | 160-162/MeOH-ether(h) | 64 |
| 1BR | CH$_3$ | 4-CH$_3$OC$_6$H$_4$ | 5,7-F | (CH$_2$)$_3$ | Morph. | NaH/DMF | HCl | 231-233/i-PrOH | 79 |
| 1BS | CH$_3$ | 4-CH$_3$OC$_6$H$_4$ | 7-F | (CH$_2$)$_3$ | Morph. | NaH/DMF | HCl | 209-211/MDC-ether | 59 |
| 1BT | CH$_3$ | 4-CH$_3$OC$_6$H$_4$ | 5-F | (CH$_2$)$_3$ | Morph. | NaH/DMF | HCl | 178-180/i-PrOH-ether | 72 |
| 1BU | CH$_3$ | 2-FC$_6$H$_4$ | — | CHCH$_3$CH$_2$CH$_2$ | Morph. | NaH/DMF | Base | 107-109 | 53 |
| 1BV | CH$_3$ | 4-CH$_3$OC$_6$H$_4$ | — | CH$_2$CHCH$_3$ | Morph. | NaH/DMF | Base | 128-130/EtOAc-hexane | 45 |
| 1BW | CH$_3$ | 2-FC$_6$H$_4$ | 5-F | CHCH$_3$CH$_2$CH$_2$ | Morph. | NaH/DMF | HCl | 124-126/EtOAc-hexane | 50 |
| 1BX | CH$_3$ | 4-CNC$_6$H$_4$ | — | CHCH$_3$CH$_2$CH$_2$ | Morph. | NaH/DMF | HCl | 160-162/MeOH-ether | 84 |
| 1BY | CH$_3$ | 4-CH$_3$OC$_6$H$_4$ | — | CHCH$_3$CH$_2$CH$_2$ | Morph. | NaH/DMF | HCl | 164-166/MeOH-ether | 24 |
| 1BZ | CH$_3$ | 4-C$_6$H$_5$OC$_6$H$_4$ | — | CH$_2$CH$_2$ | Morph. | K$_2$CO$_3$/DMF | Base | 131.5-133/CH$_3$CN | 59 |
| 1CA | CH$_3$ | 2,3-OCH$_2$OC$_6$H$_3$ | — | CH$_2$CH$_2$ | Morph. | K$_2$CO$_3$/DMF | Base | 173-174/CHCl$_3$ | 81 |
| 1CB | CH$_3$ | 2-C$_6$H$_5$C$_6$H$_4$ | — | CH$_2$CH$_2$ | Morph. | K$_2$CO$_3$/DMF | HCl | 130-138/ether | 96 |
| 1CC | CH$_3$ | 4-CNC$_6$H$_4$ | — | CH$_2$CH$_2$ | Morph. | NaH/DMF | HCl.½H$_2$O | 212-214/MeOH | 44 |
| 1CD | CH$_3$ | 2-FC$_6$H$_4$ | — | CHCH$_3$CH$_2$CH$_2$ | Morph. | NaH/DMF | HCl.¼H$_2$O | 147-150/MDC-ether | 36 |
| 1CE | CH$_3$ | 2-naphthyl | — | CH$_2$CH$_2$ | N(C$_2$H$_5$)$_2$ | NaH/DMF | Base | 106-107/EtOAc | 34 |
| 1CF | CH$_3$ | 4-CH$_3$OC$_6$H$_4$ | — | (CH$_2$)$_3$ | Pyr. | NaH/DMF | CH$_3$SO$_3$H | 152-153/i-PrOH | 77 |
| 1CG | CH$_3$ | 4-CH$_3$OC$_6$H$_4$ | — | (CH$_2$)$_3$ | Pyr. | NaH/DMF | CH$_3$SO$_3$H | 125-126/i-PrOH | 70 |
| 1CH | H | C$_6$H$_5$ | — | (CH$_2$)$_5$ | Morph. | NaH/DMF | Base | 65-67 | 43 |
| 1CI | CH$_3$ | 4-CH$_3$OC$_6$H$_4$ | 5-F | (CH$_2$)$_4$ | Morph. | NaH/DMF | HCl | 175-176/EtOH-ether | 11 |
| 1CJ | CH$_3$ | 4-CH$_3$OC$_6$H$_4$ | 5-F | (CH$_2$)$_2$ | Morph. | NaH/DMF | HCl | 214-216/EtOH-ether | 30 |
| 1CK | CH$_3$ | 2,3-F$_2$C$_6$H$_3$ | — | (CH$_2$)$_2$ | Morph. | NaH/DMF | Base | 165-167/MDC | 37 |
| 1CL | CH$_3$ | 2,6-(CH$_3$)$_2$C$_6$H$_3$ | — | (CH$_2$)$_2$ | Morph. | NaH/DMF | HCl | 275-280 | 100 |
| 1CM | CH$_3$ | 2,3-(CH$_3$O)$_2$C$_6$H$_3$ | — | (CH$_2$)$_2$ | Morph. | NaH/DMF | Base | 126-128 | 77 |
| 1CN | CH$_3$ | 3,5-(CH$_3$O)$_2$C$_6$H$_3$ | — | (CH$_2$)$_2$ | Morph. | NaH/DMF | Base | 88-90 | 64 |
| 1CO | CH(CH$_3$)$_2$ | 4-CH$_3$OC$_6$H$_4$ | — | (CH$_2$)$_2$ | Morph. | NaH/DMF | HCl | 151-153/EtOAc-ether | 42 |
| 1CP | CH(CH$_3$)$_2$ | 4-CH$_3$OC$_6$H$_4$ | 5-F | (CH$_2$)$_3$ | Morph. | NaH/DMF | Base | 90-92 | 42 |
| 1CQ | CH$_3$ | 4-NO$_2$C$_6$H$_4$ | — | (CH$_2$)$_2$ | Morph. | K$_2$CO$_3$/DMF | Base | 173-175 | 49 |

TABLE 1-continued

| Example | R₂ | R₃ | R₄ | Alk | N=B | Cat./Solv. | Base/Salt | m.p./Solv. | Yield |
|---|---|---|---|---|---|---|---|---|---|
| ICR | CH₃ | 1-naphthyl | — | (CH₂)₃ | Morph. | NaH/DMF | Base | 135–138/ether | 50 |

(c)The corresponding methanesulfonate has m.p. 162–164 (from isopropanol-ether); the hydrochloride, m.p. 178–182 (from water); the fumarate, m.p. 184–187 (from methanol-ether); and the maleate, 146–149 (from methanol ether). A higher melting polymorph of the maleate, m.p. 163–166, was obtained on crystallization from methanol alone.
(d)Consists of a 4:1 mixture of the 4-fluoro and 6-fluoro isomers.
(e)Contains 0.4 mole of isopropanol.
(f)Prepared by reaction of 4-(2-tosyloxypropyl) morpholine with appropriate indole.
(g)Prepared by reaction of 4-(bromopropyl)morpholine with appropriate indole.
(h)A higher melting polymorph of the hydrochloride has m.p. 217–218 from isopropanol.

From the Compounds of Formula III

Example 2A

To a stirred, refluxing solution of 13.2 g. (0.054 mole) of 1-[1-methyl-2-(4-morpholinyl)ethyl]-1H-indole (Preparation 5B) in 150 ml. of ethylene dichloride was added, over a period of about one hour, a mixture of 17.35 g. (0.13 mole) of aluminum chloride and 10.08 g. (0.065 mole) of 4-methylbenzoyl chloride in 200 ml. of ethylene dichloride. When addition was complete, the mixture was heated under reflux under a nitrogen atmosphere for three and a half hours and then poured, with stirring, into 1 liter of ice and water containing 300 ml. of 5N sodium hydroxide. The mixture was transferred to a separatory funnel, the organic layer was separated, and the aqueous layer was washed with an additional 300 ml. of ethylene dichloride. The combined organic extracts were then washed with brine, filtered, dried over magnesium sulfate, filtered again and evaporated to dryness to give a viscous oil (22.55 g.) which solidified on cooling. The latter was recrystallized, after charcoaling, from isopropanol to give 15.78 g. (81%) of 3-(4-methylbenzoyl)-1-[1-methyl-2-(4-morpholinyl)ethyl]-1H-indole, m.p. 116.5°–1118° C.

Examples 2B–2BI

Following a procedure similar to that described in Example 2A above, the following species of formula I in Table 2 below were prepared by reaction of a 2-$R_2$-1-aminoalkyl-1H-indole of formula III with an appropriate acid chloride ($R_3$CO-Cl) in the presence of aluminum chloride. The solvent used to carry out the reaction, methylene dichloride (MDC) or ethylene dichloride (EDC), is given in the column headed "Solv."

TABLE 2

| Example | $R_2$ | $R_3$ | $R_4$ | Alk | N=B | Solv. | Base/Salt | m.p./Solv. | Yield |
|---|---|---|---|---|---|---|---|---|---|
| 2B | $CH_3$ | 4-$CH_3C_6H_4$ | — | $CHCH_3CH_2$ | Morph. | EDC | Base | 163–165/i-PrOH | 69 |
| 2C | $CH_3$ | 2-$FC_6H_4$ | — | $CHCH_3CH_2$ | Morph. | EDC | Base | 126–128/i-PrOH | 62 |
| 2D | H | 4-$FC_6H_4$ | — | $CHCH_3CH_2$ | Morph. | EDC | Base | 153–155/i-PrOH | 83 |
| 2E | H | 2-$FC_6H_4$ | — | $CHCH_3CH_2$ | Morph. | EDC | Base | 145–147/i-PrOH | 65 |
| 2F | H | N—$CH_3$-2-pyrrolyl | — | $CHCH_3CH_2$ | Morph. | EDC | HCl | 142–144/i-PrOH | 20 |
| 2G | $CH_3$ | 4-$FC_6H_4$ | — | $CHCH_3CH_2$ | Morph. | EDC | Base | 95–98/heptane | 23 |
| 2H | $CH_3$ | N—$CH_3$-2-pyrrolyl | — | $CHCH_3CH_2$ | Morph. | EDC | Base | 143–145/i-PrOH | 32 |
| 2I | $CH_3$ | 4-$CH_3OC_6H_4$ | — | $CHCH_3CH_2$ | Morph. | EDC | Base(i) | yellow-orange powder | 13 |
| 2J | H | $C_6H_5$ | 7-$CH_3$ | $CHCH_3CH_2$ | Morph. | EDC | HCl.½$C_2H_5$OH | amorphous, off white solid | 62 |
| 2K | $CH_3$ | 4-$NO_2C_6H_4$ | — | $CHCH_3CH_2$ | Morph. | EDC | Base | oil | 59 |
| 2L | $CH_3$ | 2-$CNC_6H_4$ | — | $(CH_2)_2$ | Morph. | MDC | maleate | 185–186 | 19 |
| 2M | $CH_3$ | 3-$CNC_6H_4$ | — | $(CH_2)_2$ | Morph. | MDC | Base | 122–124 | 26 |
| 2N | $CH_3$ | N—$CH_3$-3-pyrrolyl | — | $(CH_2)_2$ | Morph. | EDC | HCl | 235–240/$CH_3$CN | 16 |
| 2O | $CH_3$ | 4-$CH_3SO_2C_6H_4$ | — | $(CH_2)_2$ | Morph. | MDC | Base | 174–175/MDC-ether | 47 |
| 2P | $CH_3$ | 3-thienyl | — | $(CH_2)_2$ | Morph. | MDC | HCl | 225–227/$H_2O$ | 39 |
| 2Q | $CH_3$ | cyclohexyl | — | $(CH_2)_2$ | Morph. | MDC | Base | 138–139/EtOH | 44 |
| 2R | $CH_3$ | 4-t-$C_4H_9C_6H_4$ | — | $(CH_2)_2$ | Morph. | MDC | HCl | 235–236 | 57 |
| 2S | $CH_3$ | 2-benzo[b]-thienyl | — | $(CH_2)_2$ | Morph. | MDC | Base | 134–135 | 23 |
| 2T | $CH_3$ | N—$CH_3$-2-pyrrolyl | — | $(CH_2)_2$ | Morph. | EDC | HCl | 238–240/acetone | 18 |
| 2U | $CH_3$ | 2-$CH_3C_6H_4$ | — | $(CH_2)_2$ | Morph. | MDC | HCl | 245–247/i-PrOH-ether | 25 |
| 2V | $CH_3$ | 3,4-$(CH_3)_2C_6H_3$ | — | $(CH_2)_2$ | Morph. | MDC | Base | 145–147/i-PrOH | 41 |
| 2W | $CH_3$ | $C_6H_5CH=CH_2$ | — | $(CH_2)_2$ | Morph. | MDC | Base | 127–128/EtOH | 29 |
| 2X | $CH_3$ | 3-benzo[b]furyl | — | $(CH_2)_2$ | Morph. | MDC | Base | 134–135/EtOH | 28 |
| 2Y | H | 2-$CH_3C_6H_4$ | — | $(CH_2)_2$ | Morph. | MDC | Base | 129–131/i-PrOH | 100 |
| 2Z | $CH_3$ | 4-$CH_3O$-cyclohexyl | — | $(CH_2)_2$ | Morph. | MDC | Base | 110–112/cyclohexane | 16 |
| 2AA | $C_2H_5$ | 4-$CH_3OC_6H_4$ | — | $(CH_2)_2$ | Morph. | MDC | Base | 143–145/EtOAc-ether | 88 |
| 2AB | Cl | 4-$CH_3OC_6H_4$ | — | $(CH_2)_2$ | Morph. | MDC | HCl | 170–173/EtOH | 58 |
| 2AC | $CH_3$ | 4-$C_3H_7C_6H_4$ | — | $(CH_2)_2$ | Morph. | MDC | Base | 86.5–87.5/EtOAc-ether | 68 |
| 2AD | $CH_3$ | 2-$CH_3C_6H_4$ | 5-F | $(CH_2)_3$ | Morph. | MDC | HCl | 215.5–219.5/EtOH | 76 |
| 2AE | $CH_3$ | 4-$FC_6H_4$ | 5-F | $(CH_2)_3$ | Morph. | MDC | HCl | 223.0–225.0/EtOH | 43 |
| 2AF | $CH_3$ | 3-furyl | 5-F | $(CH_2)_3$ | Morph. | MDC | HCl | 211.0–214.0/EtOH | 46 |
| 2AG | $CH_3$ | $C_6H_5CH=CH$ | 5-F | $(CH_2)_3$ | Morph. | MDC | HCl | 223.5–226.5/MeOH | 44 |
| 2AH | $CH_3$ | 2,4-$F_2C_6H_3$ | — | $(CH_2)_2$ | Morph. | MDC | Base | 118–120/i-PrOH | 24 |
| 2AI | $CH_3$ | 2-$FC_6H_4$ | — | $CHC_2H_5CH_2$ | Morph. | MDC | Base | 162–165/EtOAc-hexane | 52 |
| 2AJ | $CH_3$ | 4-$CH_3OC_6H_4$ | — | $CHC_2H_5CH_2$ | Morph. | MDC | HCl | 153–157/i-PrOH-ether | 39 |
| 2AK | $CH_3$ | 1-naphthyl | — | $CHCH_3CH_2$ | Morph. | EDC | Maleate | 87/t-butyl methyl ether | 36 |
| 2AL | H | 1-naphthyl | — | $(CH_2)_2$ | Morph. | EDC | Base | 105–107/ether | 44 |
| 2AM | $CH_3$ | 5-benzo[b]furyl | — | $(CH_2)_2$ | Morph. | MDC | Base | 165.5–167/EtOAc-acetone | 46 |
| 2AN | $CH_3$ | 2,4-$F_2C_6H_3$ | — | $(CH_2)_2$ | Morph. | MDC | Base | 121–123.5/i-PrOH | 30 |
| 2AO | $CH_3$ | 2,4-$F_2C_6H_3$ | 5-F | $(CH_2)_3$ | Morph. | EDC | HCl | 212–216/EtOH | 33 |
| 2AP | $CH_3$ | 2-F-4-$CH_3OC_6H_3$ | — | $(CH_2)_2$ | Morph. | EDC | HCl | 258–260/EtOH | 25 |
| 2AQ | $CH_3$ | 2-F-4-$CH_3OC_6H_3$ | 5-F | $(CH_2)_3$ | Morph. | MDC | HCl | 221–223.5/EtOH | 16 |
| 2AR | $CH_3$ | 4-$BrC_6H_4$ | 5-F | $(CH_2)_3$ | Morph. | MDC | HCl | 238–240/i-PrOH | 64 |
| 2AS | $CH_3$ | 2,6-$F_2C_6H_3$ | — | $(CH_2)_2$ | Morph. | EDC | Base | 117–119/EtOAc | 53 |
| 2AT | $CH_3$ | 2,3-$(CH_3)_2C_6H_3$ | — | $(CH_2)_2$ | Morph. | EDC | HCl.¼$H_2O$ | 241–243/EtOH | 35 |
| 2AU | $CH_3$ | 3,5-$Cl_2C_6H_3$ | — | $(CH_2)_2$ | Morph. | MDC | Base | 145–146 | 55 |
| 2AV | $CH_3$ | 3,5-$(CH_3)_2C_6H_3$ | — | $(CH_2)_2$ | Morph. | MDC | Base | 142–144/EtOH-hexane | 51 |
| 2AW | $CH_3$ | 3-$CH_3C_6H_4$ | — | $(CH_2)_2$ | Morph. | MDC | Base | 125–127 | 44 |
| 2AX | $CH_3$ | 3-$ClC_6H_4$ | — | $(CH_2)_2$ | Morph. | MDC | Base | 116–118/EtOAc-ether | 38 |
| 2AY | $CH_3$ | 3-$FC_6H_4$ | — | $CHCH_3CH_2$ | Morph. | EDC | Base | 85–87 | 27 |
| 2AZ | $CH_3$ | 2-$ClC_6H_4$ | — | $CHCH_3CH_2$ | Morph. | EDC | HCl | 150(dec.)/EtOAc | 37 |
| 2BA | $CH_3$ | 1-naphthyl | 7-$CH_3O$ | $(CH_2)_2$ | Morph. | EDC | Base | 225–227/EtOAc-ether | 11 |
| 2BB | $CH_3$ | 2-$FC_6H_4$ | 5-F | $(CH_2)_3$ | Morph. | MDC | HCl | 224–226/EtOH | 20 |
| 2BC | $CH_3$ | 3-furyl | — | $(CH_2)_2$ | Morph. | MDC | HCl | 243–245/EtOH-ether | 21 |
| 2BD | $CH_3$ | 2-$FC_6H_4$ | 5-F | $CHCH_3CH_2$ | Morph. | MDC | HCl | 208–211/EtOAc | 49 |
| 2BE | $CH_3$ | 4-$BrC_6H_4$ | — | $(CH_2)_2$ | Morph. | EDC | HCl.¼$H_2O$ | 257–260 | 13 |
| 2BF | $CH_3$ | 5-(1H-benzimid- | — | $(CH_2)_2$ | Morph. | MDC | Base | 173.5–175.5/EtOAc | 25 |

TABLE 2-continued

| Example | $R_2$ | $R_3$ | $R_4$ | Alk | N=B | Solv. | Base/Salt | m.p./Solv. | Yield |
|---|---|---|---|---|---|---|---|---|---|
| | | azolyl) | | | | | | | |
| 2BG | $CH_3$ | 4-Br-1-naphthyl | — | $(CH_2)_2$ | Morph. | MDC | Base | 126.5–128.5/EtOAc-ether | 35 |
| 2BH | H | 4-$CH_3OC_6H_4$ | — | $CHCH_3CH_2$ | Morph. | EDC | HCl.$H_2O$ | 140 | 54 |
| 2BI | $CH_3$ | 2-naphthyl | — | $CHC_2H_5CH_2$ | Morph. | MDC | $CH_3SO_3H$ | 214–216/i-PrOH | 32 |

(i) The hydrochloride has m.p. 193-197 (from methanol-t-butyl methyl ether).

C. From the Compounds of Formula VI

Example 3A

A solution of 10 g. (0.022 mole) of 2-methyl-3-(4-methoxybenzoyl)-1-[2-(p-toluenesulfonyloxy) ethyl]-1H-indole (Preparation 7A) and 8.74 g. (0.086 mole) of 4-hydroxypiperidine in 50 ml. of dry acetonitrile was heated under reflux for about forty eight hours, and the mixture was then diluted with ethyl acetate and washed with water. The organic layer was extracted with 2N hydrochloric acid, then with water, and the combined aqueous washings were combined, basified with 10% sodium hydroxide and extracted with ethyl acetate. The combined organic extracts were dried over magnesium sulfate, filtered and concentrated to dryness to give the product, in the form of the free base, as a brown oil. The latter was converted to the hydrochloride salt in ethyl acetate and ethereal hydrogen chloride to give 2.6 g. (27%) of 2-methyl-3-(4-methoxybenzoyl)-1-[2-(4-hydroxy-1-piperidinyl)ethyl]-1H-indole hydrochloride hemihydrate, m.p. 226°–229° C.

Examples 3B–3AM

Following a procedure similar to that described in Example 3A above, the following species of formula I in Table 3 below were prepared by reaction of a 2-methyl-3-$R_3$-carbonyl-1-(2-tosyloxyethyl)-1H-indole or a 2methyl-3-$R_3$-carbonyl-1-(halo-lower-alkyl)-1H-indole of formula VI with an appropriate amine, HN=B, where $R_2$, in each instance, is $CH_3$. The starting material in each of Examples 3B–3V, 3AK and 3AM was the corresponding 1-(2-tosyloxyethyl)-1H-indole; in Example 3W the corresponding 1-(3-chloropropyl)-1H-indole; and in each of Examples 3X–3AJ and 3AL the corresponding 1-(bromo-lower-alkyl)-1H-indole.

TABLE 3

| Example | $R_3$ | $R_4$ | Alk | N=B | Solv. | Base/Salt | m.p./Solv. | Yield |
|---|---|---|---|---|---|---|---|---|
| 3B | 4-$CH_3OC_6H_4$ | — | $(CH_2)_2$ | 3-HO-1-piperidinyl | $CH_3CN$ | HCl.½$H_2O$(j) | 160 | 31 |
| 3C | 4-$CH_3OC_6H_4$ | — | $(CH_2)_2$ | 4-$CH_3$-1-piperazinyl | $CH_3CN$ | Base | 110–112 | 28 |
| 3D | 4-$C_2H_5C_6H_4$ | — | $(CH_2)_2$ | 3-HO-1-piperidinyl | $CH_3CN$ | Base | 139–141 | 57 |
| 3E | 4-$CNC_6H_4$ | — | $(CH_2)_2$ | 3-HO-1-piperidinyl | DMF | HCl | 225–227/MeOH-ether | 59 |
| 3F | 4-$CH_3OC_6H_4$ | — | $(CH_2)_2$ | 3-HO-1-pyrrolidinyl | DMF | HCl | 188–190/i-PrOH | 65 |
| 3G | 4-$CH_3OC_6H_4$ | — | $(CH_2)_2$ | $N(CH_2CH_2OH)_2$ | DMF | Base | 105–107/EtOAc | 30 |
| 3H | 1-naphthyl | — | $(CH_2)_2$ | 3-HO-1-piperidinyl | DMF | HCl.$H_2O$. 1/6 i-PrOH | 175–180/i-PrOH-ether | 24 |
| 3I | 1-naphthyl | — | $(CH_2)_2$ | 1-piperazinyl | DMSO | 2HCl | 237.5–241/MeOH | 38 |
| 3J | 1-naphthyl | — | $(CH_2)_2$ | 4-$CH_3$-1-piperazinyl | DMF | 2HCl.½$H_2O$ | 195.5–199.5/MeOH | 27 |
| 3K | 4-$CH_3OC_6H_4$ | — | $(CH_2)_2$ | $NHC_2H_5$ | DMF | maleate | 180–181/EtOH | 50 |
| 3L | 4-$CH_3OC_6H_4$ | — | $(CH_2)_2$ | $NHCH_2CH_2OCH_3$ | DMF | maleate | 166–168/EtOH | 47 |
| 3M | 1-naphthyl | — | $(CH_2)_2$ | 2-$CH_3$-4-morpholinyl | DMF | Base | 144–145/ether | 21 |
| 3N | 4-$CH_3OC_6H_4$ | — | $(CH_2)_2$ | 3-$CH_3CONH$-1-piperidinyl | DMF | Base | 122–130/EtOAc | 32 |
| 3-O | 4-$CH_3OC_6H_4$ | — | $(CH_2)_2$ | $N(CH_3)CH_2CH_2OH$ | DMF | maleate | 137.5–140/MeOH-ether | 21 |
| 3P | 4-$CH_3OC_6H_4$ | — | $(CH_2)_2$ | 2-$CH_3$-4-morpholinyl | DMF | maleate.½EtOAc | 135–140/EtOAc | 52 |
| 3Q | 4-$CH_3OC_6H_4$ | — | $(CH_2)_2$ | 2-cyclohexylmethyl-1-piperidinyl | DMF | maleate | 209.5–210.5/$CH_3CN$ | 42 |
| 3R | 4-$CH_3OC_6H_4$ | — | $(CH_2)_2$ | 2,6-di-$CH_3$-4-morpholinyl | DMF | maleate | 162–162.5/acetone | 36 |
| 3S | 4-$CH_3OC_6H_4$ | — | $(CH_2)_2$ | 4-CHO-1-piperazinyl(k) | DMF | Base | 163–165/EtOAc | 43 |
| 3T | 4-$CH_3OC_6H_4$ | — | $(CH_2)_2$ | 1-(1,4-diazepinyl)(l) | DMF | 2$CH_3SO_3H$ | 200–202 | 100 |
| 3U | 4-$CH_3OC_6H_4$ | — | $(CH_2)_2$ | Thiomorph. | DMF | Base | 124–125/EtOAc | 50 |
| 3V | 4-$CH_3OC_6H_4$ | — | $(CH_2)_2$ | Thiomorph.-S,S-dioxide | DMF | maleate | 181–182/$CH_3CN$ | 15 |
| 3W | 4-$CH_3OC_6H_4$ | 5-F | $(CH_2)_3$ | 3-HO-1-piperidinyl | DMF | HCl | 126–128/MeOH-ether | 69 |
| 3X | 1-naphthyl | — | $(CH_2)_3$ | 1-pyrrolidinyl | DMF | HCl.½$H_2O$ | 150–157/acetone | 78 |
| 3Y | 4-$CH_3OC_6H_4$ | 5-F | $(CH_2)_3$ | 2-$CH_3$-4-morpholinyl | DMF | HCl | 216–217/i-PrOH | 85 |
| 3Z | 4-$CH_3OC_6H_4$ | — | $(CH_2)_3$ | 1-piperidinyl | DMF | HCl | 201–203/i-PrOH-ether | 80 |
| 3AA | 4-$CH_3OC_6H_4$ | — | $(CH_2)_3$ | 4-morpholinyl | DMF | HCl | 208–211/$CH_3CN$-ether | 43 |
| 3AB | 4-$CH_3OC_6H_4$ | — | $(CH_2)_4$ | 1-piperidinyl | DMF | HCl | 238–241/$CH_3CN$-ether | 24 |
| 3AC | 4-$CH_3OC_6H_4$ | — | $(CH_2)_4$ | 1-pyrrolidinyl | DMF | HCl | 181–183/$CH_3CN$-ether | 36 |
| 3AD | 4-$CH_3OC_6H_4$ | — | $(CH_2)_4$ | $N(C_2H_5)_2$ | DMF | HCl | 176–177/$CH_3CN$-ether | 50 |
| 3AE | 4-$CH_3OC_6H_4$ | — | $(CH_2)_3$ | $N(C_2H_5)_2$ | DMF | HCl | 179–181/$CH_3CN$ | 11 |
| 3AF | 4-$CH_3OC_6H_4$ | 5-F | $(CH_2)_3$ | Thiomorph. | DMF | HCl | 238–241 | 84 |
| 3AG | 4-$CH_3OC_6H_4$ | 5-F | $(CH_2)_3$ | $NHC_2H_5$ | DMF | p-Tosylate | 149–150/EtOH | 28 |
| 3AH | 4-$CH_3OC_6H_4$ | 5-F | $(CH_2)_3$ | Thiomorph.-S,S-dioxide | DMF | HCl | 153–155/EtOH | 54 |
| 3AI | 4-$CH_3OC_6H_4$ | 5-F | $(CH_2)_3$ | 4-$CH_3$-1-piperazinyl | DMF | maleate | 195–197/MeOH | 100 |
| 3AJ | 4-$CH_3OC_6H_4$ | 5-F | $(CH_2)_3$ | $N(CH_3)CH_2CH_2OH$ | DMF | Base | 118–120/EtOAc | 100 |
| 3AK | 4-$CH_3OC_6H_4$ | — | $(CH_2)_2$ | $N(CHO)CH_2CH_2OH$(k) | DMF | Base | glass | 81 |
| 3AL | 4-$CH_3OC_6H_4$ | 5-F | $(CH_2)_3$ | 4-CHO-1-piperazinyl | DMF | Base | oil | 31 |
| 3AM | 1-naphthyl | — | $(CH_2)_2$ | 1-piperidinyl | DMF | Base | 119–121/EtOH | 32 |

(j) The anhydrous hydrochloride has m.p. 224-226 (from ethanol).
(k) The product became formylated at the secondary amine group of the N=B function by the DMF solvent under the reaction conditions used.
(l) 1,4-Diazepine used as the H—N=B reactant. As in Example 3S, the product became formylated on the 4-position of the diazepine by the DMF solvent. The crude 4-formyl product was then saponified by heating for six hours in a solution of 6.14 g. of sodium hydroxide in 300 ml. of ethanol and 240 ml. of water.

D. Miscellaneous Processes

Example 4A

Following a procedure similar to that described in Preparation 3 above, 8.0 g. (0.02 mole) of 2-methyl-3-(3-nitrobenzoyl)-1-[2-(4-morpholinyl) ethyl]-1H-indole (Example 1AD) in 175 ml. of ethyl acetate and 75 ml. of acetic acid was reduced with hydrogen in a Parr shaker over 0.3 g. of platinum oxide. The product was isolated in the form of the free base and recrystallized from ethyl acetate to give 6.0 g. (83%) of 2-methyl-3-(3-aminobenzoyl)-1-[2-(4-morpholinyl)ethyl]-1H-indole, m.p. 167°–169° C.

Example 4B

Following a procedure similar to that described in Example 4A above, 28 9. (0.07 mole) of 2-methyl-3-(4-nitrobenzoyl)-1-[2-(4-morpholinyl) ethyl]-1H-indole (Example 1CQ) in 100 ml. of 9 1acial acetic acid and 100 ml. of ethyl acetate was reduced with hydrogen over platinum oxide and the product, in the form of the free base, was recrystallized from ethyl acetate to give 19.05 g. (75%) of 2-methyl-3-(4-aminobenzoyl)-1-[2-(4-morpholinyl) ethyl]-1H-indole, m.p. 154°–156° C.

A small amount of the free base was reacted with methanesulfonic acid and the product recrystallized from ethanol to give the corresponding methanesulfonate as an orange powder, m.p. 221°–223° C.

Example 4C

To a stirred suspension of 2.5 g. (0.0059 mole) of 2-methyl-3-(4-nitrobenzoyl)-6-methoxy-1-[2-(4-morpholinyl)ethyl]-1H-indole (Example 1AN) and 2 g. (0.036 mole) of iron filings in 25 ml. of 50% aqueous ethanol in a three-necked flask equipped with a reflux condenser and a stirrer was added, over a five minute period with stirring, 0.93 ml. of a solution containing 5 ml. of concentrated hydrochloric acid in 25 ml. of 50% aqueous ethanol. When addition was complete, the reaction mixture was heated under reflux for two and a half hours, then cooled and made basic with 15% alcoholic potassium hydroxide solution. The mixture was filtered, the filtrate was taken to dryness in vacuo, and the oily product was dissolved in methylene dichloride and the organic solution washed first with alkali, then with water and then with brine and dried over magnesium sulfate. Filtration of the solution and concentration to dryness afforded an oil which, on trituration with ethyl acetate/diethyl ether, crystallized to give 1.4 g. (71%) of 2-methyl-3-[4-aminobenzoyl)-6-methoxy-1-[2-(4-morpholinyl)ethyl]-1H-indole, m.p. 126°–128° C.

Example 4D

Following a procedure similar to that described in Example 4C above, 7.3 g. (0.018 mole) of 2-methyl 3-(4-nitrobenzoyl)-1-[1-methyl-2-(4-morpholinyl)ethyl]-1H-indole (Example 2K), dissolved in 75 ml. of 50% ethanol, was reduced with 6 g. (0.11 mole) of iron filings and 2.8 ml. of a solution containing 5.2 ml. of concentrated hydrochloric acid in 25 ml. of 50% ethanol. The product was isolated in the form of the free base to give 3.7 g. (54%) of 2-methyl-3-(4-aminobenzoyl)-1-[1-methyl-2-(4-morpholinyl)ethyl]-1H-indole, m.p. 192°–195° C.

Example 5A

To a solution of 4.0 g. (0.01 mole) of 2-methyl-3-(4-aminobenzoyl)-1-[2-(4-morpholinyl)ethyl]-1H-indole (Example 4B) in 20 ml. of glacial acetic acid was added 2.3 ml. (0.023 mole) of acetic anhydride and 2 drops of concentrated sulfuric acid. The mixture was warmed slightly, then poured into water and the aqueous mixture basified by addition of 10% sodium hydroxide. The gum which separated was isolated by decantation, triturated with water to produce a solid material which was collected and recrystallized from ethyl acetate to give 2.3 g. (56%) of 2-methyl3-(4-acetylaminobenzoyl)-1-[2-(4-morpholinyl)ethyl]-1H-indole, m.p. 173.5°–174.5° C.

Examples 5B–5F

Following a procedure similar to that described in Example 5A above, the following compounds of formula I in Table 5 below were prepared by acylation of an appropriate 2-methyl-3-(aminobenzoyl)-1-aminoalkyl-1H-indole. In each instance, $R_2$ is $CH_3$; $R_4$ is hydrogen; Alk is $(CH_2)_2$; and N=B is 4-morpholinyl. All compounds were isolated and characterized as the free bases. The acylating agent and the reaction solvent are given in the column headed "AcX/Solv."

TABLE 5

| Example | $R_3$ | AcX/Solv. | m.p./Solv. | Yield |
|---|---|---|---|---|
| 5B | 3-$CH_3CONHC_6H_4$ | $Ac_2O$/HOAc | 165–166/toluene | 44 |
| 5C | 4-$CF_3CONHC_6H_4$ | $(CF_3CO)_2O$/MDC | 170–172/toluene | 38 |
| 5D | 4-$C_6H_5CONHC_6H_4$ | $C_6H_5COCl$/MDC(m) | 148–149/MeOH | 69 |
| 5E | 4-$CH_3SO_2NHC_6H_4$ | $CH_3SO_2Cl$/MDC(n) | 225–227/MeOH(o) | 14 |
| 5F | 4-$C_2H_5CONHC_6H_4$ | $C_2H_5COCl$/HOAc | 144–145/EtOAc | 13 |

(m) Potassium carbonate used as acid acceptor.
(n) Triethylamine used as acid-acceptor.
(o) Corresponds to the trihydrate.

Example 6

Following a procedure similar to that described in Preparation 3 above, 14.0 g. (0.03 mole) of 2-methyl-3-(4-benzyloxybenzoyl)-1-[2-(4-morpholinyl)ethyl]-1H-indole (Example 1AG) in 250 ml. of ethanol was reduced with hydrogen in a Parr shaker over 1.0 g. of 5% palladium-on-charcoal. The product was converted to the hydrochloride salt which was recrystallized from water to give 11.1 g. (92%) of 2-methyl-3-(4-hydroxybenzoyl)-1-[2-(4-morpholinyl)ethyl]-1H-indole hydrochloride, m.p. 286°–288° C.

Example 7

A mixture of 7.5 g. (0.02 mole) of 2-methyl-3-(4-cyanobenzoyl)-1-[2-(4-morpholinyl)ethyl]-1H-indole (Example 1AF), 100 ml. of ethanol, 15 ml. of liquid ammonia and 2 tablespoons of a Raney nickel in ethanol suspension was heated in an autoclave at 50° C. under an initial hydrogen pressure of 320 p.s.i.g. The mixture was then cooled, the catalyst was removed by filtration, and the solution was taken to dryness in vacuo to give 7.2 g. of product as a green foamy material which was converted to the hydrochloride salt to give 1.7 g. (19%) of 2-methyl-3-(4-aminomethylbenzoyl)-1-[2-(4-morpholinyl)ethyl]-1H-indole dihydrochloride, m.p. 196°–208° C.

Example 8A

A mixture of 10.4 g. (0.023 mole) of 2-methyl-3-[4-(N-trifluoroacetylamino)benzoyl]-1-[2-(4-morpholinyl)ethyl]-1H-indole (Example 5C), 20 g. (0.20 mole) of potassium carbonate and 5 ml. (11.4 g., 0.08 mole) of methyl iodide in 100 ml. of acetone was heated under reflux with stirring for two hours and then taken to dryness to yield a yellow foam, which was partitioned between water and chloroform and extracted twice with chloroform. The combined extracts were washed with brine, filtered and taken to dryness to give a yellow oil which was dissolved in isopropanol and treated with excess hydrogen chloride followed by additional isopropanol. The solution was diluted with ether, and the solid which separated was collected and dried to give 4.6 g. of 2-methyl-3-[4-(N-methyl-N-trifluoroacetylamino)benzoyl]-1-[20(4-morpholinyl)-ethyl]-1H-indole hydrochloride, m.p. 224°–226° C.

The latter (3.7 g., 0.007 mole) was mixed with 25 ml. of 10% sodium hydroxide, and the mixture was heated under reflux for one hour. On cooling, a solid separated from the mixture which was collected, dissolved in isopropanol and treated with excess hydrogen chloride and isopropanol. The solid which separated was collected and recrystallized from methanol/diethyl ether to give 1.2 g. (37%) of 2-methyl-3-(4-methylaminobenzoyl)-1-[2-(4-morpholinyl)-ethyl]-1H-indole dihydrochloride hemihydrate, m.p. 190°–192° C.

Example 8B

Following a procedure similar to that described in Example 8A, 22 g. (0.049 mole) of 2-methyl-3-[4-(N-trifluoroacetylamino)benzoyl]-1-[2-(4-morpholinyl)ethyl]-1H-indole (Example 5C) was reacted with 35.9 g. (0.129 mole) of butyl iodide in 250 ml. of acetone in the presence of 48 g. (0.343 mole) of potassium carbonate and the resulting 2-methyl-3-[4-(N-butyl-N-trifluoroacetylamino)benzoyl]-1-[2-(4-morpholinyl)ethyl]-1H-indole (24 g., 98%) hydrolyzed by refluxing in a solution of 500 ml. of 10% sodium hydroxide and 100 ml. of ethanol. The resulting crude product was chromatographed on silica gel, eluting with 25% acetone-hexane. The higher $R_f$ material was collected and dried to give 2.6 g. of 2-methyl-3-(4-butylaminobenzoyl)-1-[2-(4-morpholinyl)ethyl]-1H-indole, m.p. 129.0°–130.0° C.

Example 9

To a stirred suspension of 12.0 g. (0.03 mole) of 2-methyl-3-(4-aminobenzoyl)-1-[2-(4-morpholinyl)ethyl]-1H-indole (Example 4B) in 15 ml. of glacial acetic acid and 30 ml. of water was added a solution of 4.5 g. (0.06 mole) of sodium isocyanate in 30 ml. of water. The mixture was stirred at room temperature for two hours, then diluted with water and made alkaline with 10% sodium hydroxide. The solid which separated was collected and recrystallized from DMF to give 5.9 g. (48%) of 2-methyl-3-(4-carbamylaminobenzoyl)-1-[2-(4-morpholinyl)ethyll]-1H-indole, m.p. 192°–202° C.

Example 10

To a stirred suspension of 3.77 g. (0.01 mole) of 2-methyl-3-(4-aminomethylbenzoyl)-1-[2-(4-morpholinyl)ethyl]-1H-indole (Example 7) in 30 ml. of toluene was added a solution of dimethyl cyanocarbonimidodithioate in 20 ml. of toluene. The mixture was stirred for an hour and a half, and the solid which separated was collected and dried to give 4.75 g. of the corresponding 3-(4-aminomethylbenzoyl)-N-(methyl cyanocarbonimidothioate).

The latter (4.0 g., 0.008 mole), in 75 ml of isopropanol and 25 ml of liquid ammonia, was heated in an autoclave for one hour at 100° C. The reaction mixture was then filtered, allowed to evaporate to dryness, and the resulting pale yellow foam was recrystallized from acetonitrile to give 2.3 g. (65%) of 2-methyl-3-(4-cyanoguanidinylmethylbenzoyl)-1-[2-(4-morpholinyl)ethyl]-1H-indole, m.p. 191.5°–195° C.

Example 11

A mixture of 10 g. (0.027 mole) of 2-methyl-3-(4-cyanobenzoyl)-1-[2-(4-morpholinyl) ethyl]-1H-indole (Example 1AF), 20 g. (0.19 mole) of sodium hypophosphite, 50 ml. of water, 50 ml. of glacial acetic acid, 100 ml. of pyridine and two spatulas of Raney nickel was heated to about 40° C. for two and a half hours and then filtered. The filtrate was taken to dryness in vacuo, and the resulting oil was washed with toluene and again concentrated to dryness to remove residual pyridine. The residual oil was suspended in aqueous alkali and extracted with ethyl acetate. The combined organic extracts was washed with brine, dried over magnesium sulfate, filtered and concentrated to dryness to give an oil which was recrystallized from ethyl acetate to afford 1.5 g. (15%) of 2-methyl-3-(4-formylbenzoyl)-1-[2-(4-morpholinyl)ethyl]-1H-indole, m.p. 149°–150° C.

Example 12

A mixture of 2.5 g. (0.006 mole) of 2-methyl-3-(4-formylbenzoyl)-1-[2-(4-morpholinyl)ethyl]-1H-indole (Example 11), 0.55 g. (0.0067 ) mole of sodium acetate and 0.51 g. (0.0073 mole) of hydroxylamine hydrochloride in 24 ml. of ethanol, 5 ml. of methanol and 6 ml. of water was heated under reflux for one hour and then concentrated to dryness in vacuo. The residual solid was collected, washed with water and diethyl ether to give 2.5 g. (95%) of 2-methyl-3-(4-oximinomethylenebenzoly)-1-[2-(4-morpoholinyl)-ethyl]-1H-indole, m.p., 184°–186° C.

Example 13A

A mixture of 20 g. (0.053 mole) of 2-methyl-3(4-methoxybenzoyl)-1-[2-(4-morpholinyl)ethyl]-1H-indole (Example 1B) and 20 g. (0.29 mole) of hydroxylamine hydrochloride in 100 ml. of pyridine was heated under reflux for about twelve hours and then diluted with methylene dichloride. The organic mixture was washed five times with water, then with brine, dried over magnesium sulfate, filtered and taken to dryness in vacuo to give a dark green oil which was washed three times with toluene and again concentrated to dryness in vacuo. Trituration of the residue with ethyl acetate/diethyl ether afforded crystals which were collected to give 9.5 g. (46%) of 2-methyl-3-(4-methoxybenzoyl)-1-[2-(4-morpholinyl)ethyl]-1H-indole oxime, m.p. 166°–169° C.

Example 13B

Following a procedure similar to that described in Example 13A above, 44 g. (0.101 mole) of 5-fluoro-3-(2-fluorobenzoyl)-2-methyl-1-[3-(4-morpholinyl)propyl]-1H-indole (Example 2BB) was reacted with 70.3 g. (1.01 moles) of hydroxylamine hydrochloride in 500 ml of pyridine and the product recrystallized from acetonitrile to give 15.5 g. (37%) of 5-fluoro-3-(2-fluorobenzoyl)-2-methyl-1-[3-(4morpholinyl)propyl]-1H-indole oxime, m.p. 150°–162° C.

Example 13C

Following a procedure similar to that described in Example 13A above, in two runs a total of 28.3 g. (0.77 mole) of 3-(2-fluorobenzoyl)-2-methyl-1-[2-(4-morpholinyl)ethyl]-1H-indole (Example 1Z) was reacted with a total of 53.7 g. (0.77 mole) of hydroxylamine hydrochloride in a total of 575 ml. of pyridine to give a total of 24.4 g. of crude product. The latter was dissolved in a solution of 54.1 g. of sodium methoxide in 500 ml. of methanol, and the solution was heated under reflux for forty-eight hours and then taken to dryness in vacuo. The residue was partitioned between chloroform and water, and the chloroformsoluble material was flash chromatographed on silica gel eluting with 98:2 chloroform:isopropanol. The slower moving material was isolated and recrystallized from toluenehexane to give 8.0 g. (33%) of (E)-3-(2-fluorobenzoyl)-2-methyl-1-[2-(4-morpholinyl)ethyl]-1H-indole oxime, m.p. 160°-167° C.

Example 14

A mixture of 8 g. (0.022 mole) of 2-methyl-3-(4-aminobenzoyl)-1-[2-(4-morpholinyl)ethyl]-1H-indole (Example 4B) and 4.28 ml. (0.033 mole) of 2,5-dimethoxytetrahydrofuran in 40 ml. of glacial acetic acid was heated under reflux for one hour and then poured into an ice/water mixture. The mixture was rendered alkaline by addition of 10% sodium bicarbonate solution, and the solid which separated was collected and dissolved in methylene dichloride. The organic solution was dried over magnesium sulfate, filtered and the filtrate concentrated to dryness in vacuo and then chromatographed through a pad of Florisil, eluting with methylene dichloride. There was thus obtained 4.5 g. of an oil which, on trituration with diethyl ether, afforded a light yellow powder which was collected to give 3.5 g. (38%) of 2-methyl-3-[4-(1H-pyrrol-1-yl) benzoyl]-1-[2-(4-morpholinyl)ethyl]-1H-indole, m.p. 125°-127° C.

Example 15

To each of three 14 liter fermentors containing 10 liters of soybean meal/dextrose medium (containing 5 g./ liter of soybean meal, 5 g./liter of brewer's yeast, 5 g./ liter of dipotassium hydrogen phosphate and 20 g./liter of dextrose) at pH 6.4, was added 2.0 g. (0.016 mole total) of 2-methyl-3-(4-methoxybenzoyl)-1-[2-(4-morpholinyl)ethyl]-1H-indole (Example 1B), and the mixtures were cultured for five days in the presence of *Fusarium solani* (Mart.) with stirring at 400 rpm at a temperature of 26°-27° C. while sparging with air at 5 liters per minute. The mixtures were then separately extracted with 20 liters of methylene dichloride using 20 liters per fermentor, and the combined extracts were concentrated to 20 liters. The concentrate was washed first with 2 liters of 0.05N sodium hydroxide, then two times with 2 liters of water, and the organic layer was concentrated to about 1 liter, dried over sodium sulfate, charcoaled, filtered and further evaporated to dryness to give an oily residue which solidified on cooling. The latter was recrystallized from acetone/diethyl ether to give 2.7 g. (43%) of 2-methyl-3-(4-methoxybenzoyl)-1-[2-(4-morpholinyl)ethyl]-1H-indole/N(MOR)-oxide, m.p. 142°-144° C.

Example 16A

A mixture of 38.3 g. (0.10 mole) of 2-methyl-3-(2-methoxybenzoyl)-1-[2-(4-morpholinyl)ethyl]-1H-indole (Example 1U) and 35.2 g. (0.31 mole) of pyridine hydrochloride was heated in an oil bath at 210° C. for four hours and the mixture allowed to cool. The solidified reaction mixture was partitioned between ethyl acetate and aqueous sodium carbonate by warming on a steam bath, and the organic layer was separated, taken to dryness and subjected to high performance liquid chromatography on a silica gel column in 1:1 hexane:ethyl acetate. The first 7 liters of eluate were discarded, and the next 8 liters were collected, taken to dryness and the residue recrystallized from isopropanol to give 8.33 g. (23%) of 2-methyl-3-(2-hydroxybenzoyl)-1-[2-(4-morpholinyl)ethyl]-1H-indole, m.p. 115°-116° C.

Example 16B

Following a procedure similar to that described in Example 16A, 15.8 g. (0.035 mole) of 5-fluoro-2-methyl-3(4-methoxybenzoyl)-1-[3-(4-morpholinyl)propyl]-1H-indole hydrochloride (Example 1I) was heated with 20.4 g. (0.176 mole) of pyridine hydrochloride at 210° C. in an oil bath for two hours, and the product isolated as the hydrochloride salt to give 9.2 g. (67%) of 5-fluoro-2-methyl-3(4-hydroxybenzoyl)-1-[3-(4-morpholinyl)propyl]-1H-indole hydrochloride, m.p. 290°-292° C. (from DMF-ether).

Example 17

A mixture of 1.9 g. (0.005 mole) of 2-methyl-3(4-aminomethylbenzoyl)-1-[2-(4-morpholinyl)ethyl]-1H-indole (Example 7), 0.7 g. (0.0025 mole) of 2-methyl-2-thiopseudourea sulfate and 10 ml of water was heated on a steam bath for two hours and then filtered. The filtrate was taken to dryness, and the residue was recrystallized from methanol to give 1.0 g. (85%) of 2-methyl-3-(4-guanidinylmethylbenzoyl)-1-[2-(4-morpholinyl)ethyl]-1H-indole sulfate (2:1), m.p. 170°-180° C.

Example 18

Following a procedure similar to that described in Preparation 3 above, a solution of 0.9 g. (0.0019 mole) of 6-benzyloxy-2-methyl-3-(4-methoxybenzoyl)-1-[2-(4-morpholinyl)ethyl]-1H-indole (Example 1BK) in 200 ml. of methanol was reduced with hydrogen over three spatulas (approximately 1.5 g.) of 10% palladium-on-charcoal under a hydrogen pressure of 50 p.s.i.g. at ambient temperature in a Parr shaker. The product was isolated in the form of the hydrochloride which was recrystallized from ethyl acetatediethyl ether to give 0.35 g. of 6-hydroxy-2-methyl-3-(4-methoxybenzoyl)-1-[2-(4-morpholinyl)ethyl]-1H-indole hydrochloride hydrate (3:4), m.p. 185°-187° C.

Example 19

To 70 ml. of dry DMF was added, dropwise with stirring, 15 ml. of phosphorus oxychloride while cooling in an ice bath. The mixture was then treated with a solution of 24.4 g. (0.10 mole) of 2-methyl-1-[2-(4-morpholinyl)ethyl]-1H-indole (Preparation 4A) in 50 ml. of DMF while continuing to cool in an ice bath. When addition was complete, the mixture was stirred for about one hour and then poured into 50 g. of ice to give a clear solution which was chilled to about 20° C. and basified by the addition of 150 ml. of 35% potassium hydroxide. The mixture was warmed to about 70°, then chilled in an ice bath, and the solid which separated was collected, dried and recrystallized from ethyl acetate to give 23.3 g. (86%) of 3-formyl-2-methyl-1[2-(4-morpholinyl) ethyl]-1H-indole, m.p. 115°-116° C.

A solution containing 13.6 g. (0.05 mole) of the latter and 9.0 g. (0.06 mole) of 4-methoxyacetophenone in 50 ml. of absolute ethanol was treated with 500 ml. of 3.7N ethanolic hydrogen chloride in a thin stream, while stirring, and the resulting red solution was stirred for twenty-four hours. The solid which separated was collected by filtration, washed with absolute ethanol and then recrystallized first from methanol and then from 50% ethanol to give 5.3 g. (24%) of 1-{2-methyl-1-[2-(4-morpholinyl)ethyl]-1H-indol-3-yl}-3-(4-methoxyphenyl)propen-3-one monohydrochloride, m.p. 259°-262° C.

Example 20A

Following a procedure similar to that described in Example 19 above, 3-acetyl-2-methyl-1-[2-(4-morpholinyl)ethyl]-1H-indole was prepared by reaction of 12 g. (0.05 mole) of 2-methyl-1-[2-(4-morpholinyl)ethyl]-1H-indole (Preparation 4A) with 10 ml. (0.11 mole) of phosphorus oxychloride in 25 ml. of dimethylacetamide. The product was dissolved in isopropanol and the solution treated with ethereal hydrogen chloride to give 6 g. (37%) of the product as the hydrochloride salt, m.p. 249°–253 ° C.

To a solution of 6 g. (0.107 mole) of potassium hydroxide pellets in 350 ml. of absolute ethanol was added 15 g. (0.047 mole) of the latter and 19 g. (0.14 mole) of 2-methylbenzaldehyde. The mixture was heated under reflux for one and a half hours, concentrated to dryness and the product, in the form of the free base, recrystallized once from ethyl acetate and once from isopropanol to give 7.9 g. (41%) of 3-(2-methylcinnamoyl)-2-methyl-1-[2-(4-morpholinyl)ethyl]-1H-indole, m.p. 131°–135° C.

Example 20B

Following a procedure similar to that described in Example 20A above, 14.75 g. (0.0516 mole) of 3-acetyl-2-methyl-1-[2-(4-morpholinyl)ethyl]-1H-indole (Example 20A) was reacted with 2-fluorobenzaldehyde in 260 ml. of ethanol in the presence of 3.44 g. (0.061 mole) of potassium hydroxide pellets and the product, in the form of the free base, recrystallized from ethyl acetate to give 10.0 g. (54%) of 3-(2-fluorocinnamoyl)-2-methyl-1-[2-(4-morpholinyl)ethyl]-1H-indole, m.p. 113°–116° C.

Example 21

A solution of 11 g. (0.025 mole) of 1-[2-(3-hydroxy-1-piperidinyl)ethyl]-2-methyl-3-(4-methoxybenzoyl)-1H-indole (Example 3B) in 50 ml. of pyridine and 25 ml. of acetic anhydride was allowed to stand at ambient temperature for about forty-eight hours and the mixture then poured into ice water. The oily solid which separated was collected, dissolved in ethyl acetate and the solution washed first with dilute sodium hydroxide, then with brine, dried and taken to dryness. The residue was dissolved in ethyl acetate, the solution treated with 3.67 g. of maleic acid, the mixture heated to boiling to dissolve all solid, then cooled, and the solid which separated was collected and recrystallized once again from ethyl acetate to give 8.12 g. (59%) of 1-[2-(3-acetoxy-1-piperidinyl)ethyl]-2-methyl-3-(4-methoxybenzoyl)-1H-indole maleate (1:1), m.p. 161°–161.5° C.

Example 22

To a stirred solution of 12.5 g. (0.03 mole) of 2-methyl-3-(4-methoxybenzoyl)-1-[2-(1-piperazinyl)ethyl]-1H-indole (Example 1L) in 150 ml. of pyridine was added, with stirring while cooling in an ice bath, 7.1 g. (0.066 mole) of ethyl chloroformate. When addition was complete, the solution was stirred in an ice bath for thirty minutes, then allowed to stand at ambient temperature for about eighteen hours and then poured into ice water. Extraction of the mixture with ethyl acetate afforded the crude product in the form of the free base which was dissolved in ethyl acetate and converted to the maleate salt by addition of 2.6 g. of maleic acid. The latter was recrystallized from ethyl acetate-ether to give 7.6 g. (41%) of 1-[2-(4-carbethoxy-1-piperazinyl)ethyl]-2-methyl-3-(4-methoxybenzoyl)-1H-indole maleate (1:1), m.p. 155°–156° C.

Example 23A

A solution of 12.5 g. (0.033 mole) of 2-methyl-3-(4-methoxybenzoyl)-1-[2-(1-piperazinyl)ethyl]-1H-indole (Example 1L) in 150 ml. of pyridine was cooled in an ice bath and treated with 50 ml. of acetic anhydride and the solution allowed to stand at ambient temperature for about eighteen hours. The solution was then poured into ice water and the mixture extracted with ethyl acetate. The organic solution, on washing with brine, drying over sodium sulfate and evaporation to dryness, afforded the crude product which was taken into ethyl acetate and the solution treated with 4.2 g. of maleic acid. The solid which separated was collected and recrystallized from ethanol to give 7.36 g. (42%) of 1-[2-(4-acetyl-1-piperazinyl)ethyl]-2-methyl-3-(4-methoxybenzoyl)-1H-indole maleate (1:1), m.p. 147.5°–152° C.

Example 23B

Following a procedure similar to that described above in Example 23A, 11.9 g. (0.029 mole) of 5-fluoro-2-methyl-3-(4-methoxybenzoyl)-1-[3-(1-piperazinyl)propyl]-1H-indole (Example 1BN) was reacted with 50 ml. of acetic anhydride in 150 ml. of pyridine and the product isolated in the form of the methanesulfonate salt to give 6.6 g. (41%) of 5-fluoro-2-methyl-3-(4-methoxybenzoyl)-1-[3-(4-acetyl-1-piperazinyl)propyl]-1H-indole methanesulfonate, m.p. 170°–171° C.

Example 24

A solution of 15 g. (0.04 mole) of 2-methyl-3-(4-aminobenzoyl)-1-[2-(4-morpholinyl)ethyl]-1H-indole (Example 4B), 12 g. (0.4 mole) of formaldehyde and 7.5 g. (0.119 mole) of sodium cyanoborohydride in 250 ml. of acetonitrile was stirred for thirty minutes and then treated dropwise with acetic acid until acidic. The mixture was stirred for about eighteen hours, then poured into aqueous potassium hydroxide and the mixture extracted with ether. The organic extracts, on drying over magnesium sulfate and concentration to dryness, afforded a yellow solid which was recrystallized from isopropanol to give 7.5 g. (48%) of 3-(4-dimethylaminobenzoyl)-2-methyl-1-[2-(4-morpholinyl)ethyl]-1H-indole, m.p. 152°–154° C.

Example 25A

A solution of 19.1 g. (0.047 mole) of 1-(3-bromopropyl)-5-fluoro-2-methyl-3-(4-methoxybenzoyl)-1H-indole (Preparation 7D) in 500 ml. of acetone and 50 ml. of water was treated with 3.05 g. (0.047 mole) of sodium azide and the mixture heated under reflux for about eighteen hours and then taken to dryness in vacuo. The residue was partitioned between ethyl acetate and water, and the organic layer separated, washed with brine, taken to dryness and the residue recrystallized from isopropanol to give 10.3 g. (60%) of 1-(3-azidopropyl)-5-fluoro-2-methyl-3-(4-methoxybenzoyl)-1H-indole, m.p. 69–73.

The latter (0.028 mole) was dissolved in 265 ml. of ethanol and 35 ml. of THF and reduced with hydrogen over 1.0 g. of 10% palladium-on-charcoal in a Parr shaker. When reduction was complete, in about four hours, the mixture was filtered, the filtrate taken to dryness and the residue dissolved in ethyl acetate and treated with 3.13 g. of maleic acid and heated to dissolve all the material. The solid which separated was collected and recrystallized from isopropanol to give 9.7 g. (76%) of 1-(3-aminopropyl)-5-fluoro-2-methyl-3-(4-methoxybenzoyl)-1H-indole maleate (1:1) m.p. 169°–171° C.

Example 25B

Following a procedure similar to that described in Example 25A above, 13.98 g. (0.03 mole) of 2-methyl-3-(4-methoxybenzoyl)-1-(2-tosyloxyethyl)-1H-indole (Preparation 7A) in 325 ml. of acetone and 32.5 ml. of water was reacted with 1.96 g. (0.03 mole) of sodium azide and the product recrystallized from isopropanol to give 6.1 g. (61%) of 1-(2-azidoethyl)-2-methyl-3-(4-methoxybenzoyl)-1H-indole, m.p. 91°–93° C.

The latter (0.024 mole), dissolved in 250 ml. of ethanol and 50 ml. of THF, was reduced with hydrogen over 0.8 g. of 10% palladium-on-charcoal at 47 p.s.i.g. and the product isolated in the form of the maleate salt to give 7.6 g. (75%) of 1-(2-aminoethyl)-2-methyl-3-(4-methoxybenzoyl) -1H-indole maleate, m.p. 165°-166° C.

Example 26A

A mixture of 10 g. (0.027 mole) of 3-(4-fluorobenzoyl)-2-methyl-1-[2-(4-morpholinyl)ethyl]-1H-indole, (Example 1Q) 2.5 g. (0.033 mole) of 2-methoxyethylamine and 7.6 g. (0.054 mole) of potassium carbonate in 15 ml. of DMSO was heated at 95° C. under nitrogen and the mixture then poured into ice water. The solid which separated was collected, dissolved in methylene dichloride and the solution washed with brine, dried over magnesium sulfate, filtered and taken to dryness in vacuo. Recrystallization of the residue from ethyl acetate-ether afforded 4.2 g. (37%) of 2-methyl-3-[4-(2-methoxyethylamino)benzoyl]-1-[2-(4-morpholinyl)ethyl]-1H-indole, m.p. 121°-123° C.

Examples 26B-26I

Following a procedure similar to that described in Example 26A above, reaction of a 3-(4-halobenzoyl)-2-methyl-1-[2-(4-morpholinyl)ethyl]-1H-indole with an appropriate amine in the presence of potassium carbonate afforded the species of formula I in Table 26 where, in each instance, $R_2$ is $CH_3$; and N=B is 4-morpholinyl. The species of Examples 26B-26D, 26G and 26H were obtained from the corresponding 4-fluorobenzoyl starting material, and the species of Examples 26E, 26F and 26I were obtained from the corresponding bromobenzoyl (or bromonaphthyl) starting materials.

m.p. 142.5°-144° C. (1.5 g., 49%), prepared by saponification of 1.6 g. (0.0026 mole) of 1-[2-(3-acetylamino-1-piperidinyl)ethyl]- 2-methyl-3-(4-methoxybenzoyl)-1H-indole (Example 3N) with 1.6 g. (0.04 mole) of sodium hydroxide in 2 ml. of water and 6 ml. of ethylene glycol; and Example 27D - 5-fluoro-2-methyl-3-(4-methoxybenzoyl)-1-[3-(1-piperazinyl)propyl]-1H-indole dimethanesulfonate, m.p. 114°-115° C. (8.7 g., 27%), prepared by saponification of 23 g. (0.053 mole) of 5-fluoro-1-[3-(4-formyl-1-piperazinyl)propyl]-2-methyl-3-(4-methoxybenzoyl)-1H-indole (Example 3AL) with 5.6 g. (0.014 mole) of sodium hydroxide in 265 ml. of ethanol and 210 ml. of water.

Example 28

To a solution containing 16.9 g. (0.044 mole) of 1(3-bromopropyl)-2-methyl-3-(4-methoxybenzoyl)-1H-indole (Preparation 7G) in 200 ml. of DMF was added 5 g. (0.088 mole) of azetidine. The mixture was stirred for about 24 hours at ambient temperature, then diluted with water and extracted with ethyl acetate. The organic extracts were washed with water, then with brine, dried over magnesium sulfate, filtered and taken to dryness. The residue was taken into ethyl acetate, the solution diluted with ethereal hydrogen chloride, and the solid which separated was collected and recrystallized repeatedly from isopropanol to give 2.0 g. (10%) of 1-[3-(3-chloropropylamino)propyl]-2-methyl-3-(4-

TABLE 26

| Example | $R_3CO$ | $R_4$ | Alk | Solv. | Base/Salt | m.p./Solv. | Yield |
|---------|---------|-------|-----|-------|-----------|------------|-------|
| 26B | 4-(3-HO-1-piperdinyl)benzoyl | — | $(CH_2)_2$ | DMSO | $2HCl.\frac{1}{2}H_2O$ | 196 | 33 |
| 26C | 4-(1-piperazinyl)benzoyl | — | $(CH_2)_2$ | DMSO | $2HCl.\frac{1}{2}H_2O$ | 240 | 52 |
| 26D | 4-(4-HO-1-piperdinyl)benzoyl | — | $(CH_2)_2$ | DMSO | $2HCl.\frac{1}{2}H_2O$ | 130/EtOH-MDC | 37 |
| 26E | 4-(1H-imidazol-1-yl)benzoyl | — | $(CH_2)_2$ | DMF | Base | 171-173/i-PrOH | 54 |
| 26F | 4-(1H-imidazol-1-yl)benzoyl | 5-F | $(CH_2)_3$ | DMF | Base | 135-137/i-PrOH | 66 |
| 26G | 4-(4-morpholinyl)benzoyl | — | $(CH_2)_2$ | DMSO | $HCl.H_2O$ | 175/EtoAc-ether | 43 |
| 26H | 4[HO(CH$_2$)$_3$NH]benzoyl | — | $(CH_2)_2$ | DMSO | Base | 122-124/EtOAc | 32 |
| 26I | 4-CN-1-naphthyl-CO(p) | — | $(CH_2)_2$ | DMF | Base | 180.5-183.5/EtOAc | 57 |

(p) Obtained from corresponding 4-bromo-1-naphthyl species (Example 2AT) and cuprous cyanide in presence of 5 drops of pyridine.

Example 27A

A mixture of 8.2 g. (0.02 mole) of 1-[2-(4-formyl-1piperazinyl)ethyl]-2-methyl-3-(4-methoxybenzoyl)-1H-indole (Example 3S) and 2.06 g. (0.052 mole) of sodium hydroxide in 100 ml. of ethanol and 80 ml. of water was heated under reflux for four hours, then poured into ice water and extracted with ethyl acetate. The organic solution was washed with brine, dried over sodium sulfate, taken to dryness and the residue dissolved in ethyl acetate. The solution was treated with an excess of a 1N solution of methanesulfonic acid, and the solid which separated was collected and recrystallized from ethanol to give 9.0 g. (79%) of 2-methyl-3-(4-methoxybenzoyl)-1-[2-(1-piperazinyl)ethyl]-1H-indole dimethanesulfonate, m.p. 240° C.

Examples 27B-27D

Following a procedure similar to that described in Example 26A above, the following species of formula I were similarly prepared:

Example 27B - 1-[2-(2-hydroxyethylamino)ethyl]-2-methyl-3-(4-methoxybenzoyl)-1H-indole, m.p. 99°-100.5° C. (14.2g., 50%), prepared by saponification of 30.8 g. (0.08 mole) of 1-[2-(N-formyl-2-hydroxyethylamino)ethyl]-2-methyl-3-(4-methoxybenzoyl) -1H-indole (Example 3AK) with 9.7 g. (0.243 mole) of sodium hydroxide in 160 ml. of water and 200 ml. of ethanol;

Example 27C - 1-[2-(3-amino-1-piperidinyl)ethyl]-2-methyl-3-(4-methoxybenzoyl)-1H-indole maleate (1:2), methoxybenzoyl)-1H-indole hydrochloride, m.p. 140°-142° C.

Example 29A

To a solution of 15.0 g. (0.032 mole) of 5-fluoro-2-methyl-3-(4-methoxybenzoyl)-1-[3-(4-thiomorpholinyl)propyl]-1H-indole hydrochloride (Example 3AF) in 195 ml. of glacial acetic acid was added 8.12 g. (0.038 mole) of an 80% solution of m-chloroperbenzoic acid, and the solution was stirred at ambient temperature for about forty-eight hours and then poured into 300 ml. of ice water. The mixture was treated with 1 g. of sodium bisulphite, basified with 35% sodium hydroxide and then extracted with chloroform. The organic extracts, on washing with water, then with brine, drying over sodium sulfate and evaporation to dryness afforded 1.9 g. of the product as the free base which was converted to the maleate salt by solution of the base in ethyl acetate and addition of one equivalent of maleic acid. The salt was recrystallized from ethanol to give 12.85 g. (72%) of 5-fluoro-2-methyl-3-(4-methoxybenzoyl)1-[3-(4-thiomorpholinyl)propyl]-1H-indole S-oxide maleate, m.p. 160°-161° C.

Examples 29B and 29C

Following a procedure similar to that described in Example 29A above, the following species of formula I were similarly prepared:

Example 29B - 2-methyl-3-(4-methoxybenzoyl)-1-[2-(4-thiomorpholinyl)ethyl]-1H-indole S-oxide maleate, m.p. 179°-180° C. (7.2 g., 82%), prepared by oxidation of 110 g. (0.028 mole) of 2-methyl-3-(4-methoxybenzoyl)-1-[2-(4-thiomorpholinyl)ethyl]-1H-indole (Example 3U) with 6.7 g. (0.03 mole) of m-chloroperbenzoic acid in 110 ml. of glacial acetic acid; and Example 29C - 2-methyl-3-(4-methoxybenzoyl)-1-[2-(4-thiomorpholinyl)ethyl]-1H-indole S,N-dioxide dihydrate, m.p. 143°-145° C. (3.9 g., 27%), prepared by oxidation of 12.0 g. (0.030 mole) of 2-methyl-3-(4-methoxybenzoyl)-1-[2-(4thiomorpholinyl)ethyl]-1H-indole (Example 3U) with 6.6 g. (0.030 mole) of m-chloroperbenzoic acid in 120 ml. of chloroform.

Example 30

A solution of 28.7 g. (0.177 mole) of benzoylacetone and 23.2 ml. (0.177 mole) of 2-(4-morpholinyl)ethylamine in 600 ml. of toluene was heated under reflux for ten and a half hours under a Dean-Stark trap and the solution then cooled and taken to dryness to give N-[2-(4morpholinyl)ethyl]-N-(1-methyl-3-oxo-3-phenyl-propenyl)amine as a yellow solid.

The latter (11.3 g., 0.41 mole) and 8.9 g. (0.082 mole) of benzoquinone in 40 ml. of nitromethane was stirred under nitrogen for forty-eight hours at room temperature and the mixture then filtered through silica gel and the filtrate adsorbed onto silica gel and flash chromatographed using 5% acetone in ethyl acetate. The product was taken off in the early and middle fractions which were taken to dryness. The product was recrystallized first from ethyl acetate and then from methanol to give 1.0 g. (7%) of 3-benzoyl-5-hydroxy-2-methyl-1-[2-(4-morpholinyl)ethyl]-1H-indole, m.p. 215°-217° C.

Example 31A

A solution of 12.4 g. (0.0395 mole) of 5-fluoro-2-methyl-3-(4-methoxybenzoyl)-1-[1-(2,3-epoxy)propyl]-1H-indole (Preparation 9A) and 4.79 g. (0.055 mole) of morpholine in 60 ml. of chloroform was heated under reflux for about forty-eight hours and then taken to dryness in vacuo. The crude product was dissolved in methylene dichloride, and the solution was treated with an excess of ethereal hydrogen chloride and then diluted with ether. The solid which separated was collected and recrystallized from methanol-ether to give 13.3 g. (61%) of 1-[2-hydroxy-3-(4-morpholinyl)-propyl]-5-fluoro-2-methyl-3-(4-methoxybenzoyl)-1H-indole hydrochloride hydrate, (1HCl.1 1 1/4H$_2$O), m.p. 143°-145° C.

Examples 31B-31-O

Following a procedure similar to that described in Example 31A above, reaction of a 1-[1-(2,3-epoxy)propyl]3-R$_3$-carbonyl-1H-indole with an amine, HN=B, afforded the following compounds of formula Ib listed in Table 31, where R$_2$ in each instance is CH$_3$.

TABLE 31

| Example | R$_3$ | R$_4$ | N=B | Solv. | Base/Salt | m.p./Solv. | Yield |
|---|---|---|---|---|---|---|---|
| 31B | 4-CH$_3$OC$_6$H$_4$ | 5-F | 1-piperidinyl | CHCl$_3$ | HCl | 219-221/MeOH-ether | 67 |
| 31C | 4-CH$_3$OC$_6$H$_4$ | 5-F | 1-pyrrolidinyl | CHCl$_3$ | HCl | 183-185/i-PrOH-ether | 76 |
| 31D | 4-CH$_3$OC$_6$H$_4$ | — | NHCH$_3$ | DMF | Base | 104.5-106.5/EtOAc-EtOH | 55 |
| 31E | 4-CH$_3$OC$_6$H$_4$ | — | NHC(CH$_3$)$_3$ | DMF | Base | 110-111.5/ether | 63 |
| 31F | 1-naphthyl | — | 1-pyrrolidinyl | DMF | Base | 161-162/EtOAc | 88 |
| 31G | 4-CH$_3$OC$_6$H$_4$ | — | Morph. | CHCl$_3$ | Base | 88-90/EtOAc-hexane | 32 |
| 31H | 4-CH$_3$OC$_6$H$_4$ | — | 1-pyrrolidinyl | CHCl$_3$ | CH$_3$SO$_3$H | 176-178/i-PrOH | 37 |
| 31I | 4-CH$_3$OC$_6$H$_4$ | — | 1-piperidinyl | CHCl$_3$ | Base | 88-90/EtOAc-hexane | 19 |
| 31J | 4-CH$_3$OC$_6$H$_4$ | — | azido | acetone | Base | 110-111/i-PrOH | 38 |
| 31K | 4-CH$_3$OC$_6$H$_4$ | — | 1-azetidinyl(q) | THF | Base | 83-86/EtOAc-hexane | 3 |
| 31L | 4-CH$_3$OC$_6$H$_4$ | — | N(CH$_3$)$_2$ | DMF | HCl | 149-151/CH$_3$CN-ether | 79 |
| 31M | 4-CH$_3$OC$_6$H$_4$ | — | NHCH(CH$_3$)$_2$ | DMF | HCl | 213-216/CH$_3$CN | 68 |
| 31N | 4-CH$_3$OC$_6$H$_4$ | — | NHCH$_2$H$_5$ | DMF | Base | 133-135/EtOAc-hexane | 55 |
| 31-O | 4-CH$_3$OC$_6$H$_4$ | — | N(C$_2$H$_5$)$_2$ | DMF | Base | 114-116/EtOAc-hexane | 75 |

(q) The azetidine in the THF was first reacted with a 20% molar excess of n-butyl lithium at 0° C., and the lithium salt thus formed was treated with the epoxide in THF.

Example 32

Following a procedure similar to that described above in Example 25A, 60 g. (0.165 mole) of 1-(3-azido-2-hydroxy-1-propyl)-2-methyl-3-(4-methoxybenzoyl)-1H-indole (Example 31J) in 500 ml. of ethanol was reduced with hydrogen over 35 g. of palladium-on-barium sulfate catalyst. The product was isolated in the form of the free base and recrystallized from ethyl acetate to give 10.2 g. (18%) of 1-(3-amino-2-hydroxy-1-propyl)-2-methyl-3-(4-methoxybenzoyl)-1H-indole, m.p. 152°-153° C.

Example 33

The hydrobromide salt of 2-methyl-3-(4-methoxybenzoyl)-1-[2-(4-morpholinyl)ethyl]-1H-indole (Example 1B) (10.0 g., 0.026 mole) was prepared by passing hydrogen bromide gas into a solution of the former in 200 ml. of MDC. The hydrobromide was isolated, redissolved in 300 ml. of MDC and the solution treated with 6.94 g. (0.039 mole) of N-bromosuccinimide. The solution was heated under reflux and irradiated with light for twenty minutes, and the solid which had separated was taken into chloroformethyl acetate and the solution extracted with aqueous potassium carbonate, dried over magnesium sulfate and taken to dryness. The residue was chromatographed on silica gel, the product being eluted with 25% acetone in toluene, which was isolated and recrystallized from toluene to give 3.7 g. (31%) of 5-bromo-2-methyl-3-(4-methylbenzoyl)-1-[2-(4morpholinyl)ethyl]-1H-indole, m.p. 134.5°-136° C.

Examples 34A-34H

Following a procedure similar to that described in Example 2A above, it is contemplated that other species of formula I as follows can be prepared by reaction of a 2-R$_2$-1-[2-(4-morpholinyl)ethyl]-1H-indole with an appropriate aroyl chloride (R$_3$COCl) in the presence of aluminum chloride in methylene dichloride:

Example 34A - 2-methyl-1-[2-(4-morpholinyl)ethyl]-3-(2-quinolinecarbonyl)-1H-indole, by reaction of 2-methyl-1-[2-(4-morpholinyl)ethyl]-1H-indole with 2-quinoline carboxylic acid chloride;

Example 34B - 2-methyl-1-[2-(4-morpholinyl)ethyl]-3-(3-quinolinecarbonyl)-1H-indole, by reaction of 2-methyl-1-[2-(4-morpholinyl)ethyl]-1H-indole with 3-quinoline carboxylic acid chloride;

Example 34C 2-methyl-1-[2-(4-morpholinyl)ethyl]-3-(4 -quinolinecarbonyl)-1H-indole, by reaction of 2-methyl-1[2-(4-morpholinyl)ethyl]-1H-indole with 4-quinoline carboxylic acid chloride;

Example 34D - 2-methyl-1-[2-(4-morpholinyl)ethyl]-3-(5-quinolinecarbonyl)-1H-indole, by reaction of 2-methyl-1-[2-(4-morpholinyl)ethyl]-1H-indole with 5-quinoline carboxylic acid chloride;

Example 34E - 2-methyl-1-[2-(4-morpholinyl)ethyl]-3-(6-quinolinecarbonyl)-1H-indole, by reaction of 2-methyl-1-[2-(4-morpholinyl)ethyl]-1H-indole with 6-quinoline carboxylic acid chloride;

Example 34F - 2-methyl-1-[2-(4-morpholinyl)ethyl]-3-(7-quinolinecarbonyl)-1H-indole, prepared by reaction of 2-methyl-1-[2-(4-morpholinyl)ethyl]-1H-indole with 7-quinoline carboxylic acid chloride;

Example 34G - 2-methyl-1-[2-(4-morpholinyl)ethyl]-3-(8-quinolinecarbonyl)-1H-indole, by reaction of 2-methyl-1-[2-(4-morpholinyl)ethyl]-1H-indole with 8-quinoline carboxylic acid chloride; and Example 34H - 2-benzoyl-1-[2-[4-morpholinyl)ethyl]-3-(4-methoxybenzoyl)-1H-indole, by reaction of 2-benzoyl-1-[2-(4-morpholinyl)ethyl]-1H-indole with 4-methoxybenzoyl chloride.

BIOLOGICAL TEST RESULTS

The 3-$R_3$-carbonyl-1-aminoalkyl-1H-indoles of formulas I, Ia and Ib of the invention were tested in the acetylcholine-induced abdominal constriction test (Ach), the anti-bradykinin test (BRDK) and the rat paw flexion test (P.F.), all in vivo tests, and were found to have analgesic activity. Data so-obtained are given in Table B below. Unless noted otherwise, all data were obtained on oral administration and are expressed either as the $ED_{50}$ or as the percent inhibition at a given dose level (thus 30/100 or 30% inhibition at 100 mg./kg.)

In some instances, the compounds were retested two or more times, and $ED_{50}$ values were calculated for each series of repeat tests. In such instances, each of the $ED_{50}$ values so-obtained is given in a series of values, thus 6, 28, 30, 43 in the case of the species of Example 1AW in the acetylcholine-induced abdominal constriction test.

TABLE B

| Example | Ach | BRDK | P.F. |
|---------|-----|------|------|
| 1A | 73 | 56 | |
| 1B | 24,50,30,37 | 8.1 (i.v.) | |
|  | 41,26,34,58 | | |
|  | 6.7 (i.v.) | | |
|  | 21,48 (s.c.) | | |
| 1C | 126 | | |
| 1D | 34,10,54,22 | 0/100 | 64 |
|  | 5.1 (i.v.) | | |
|  | 49 (s.c.) | | |
| 1E | 0/100 | | |
| 1F | 20 | 0/200 | 88/100 |
|  | 13 (i.v.) | | |
| 1G | 84 | | |
|  | 0/3 (i.v.) | | |
|  | 50/10 (i.v.) | | |
|  | 100/30 (i.v.) | | |
| 1H | 33/100 | | |
|  | 71/300 | | |
|  | 0/3 (i.v.) | | |
|  | 30/10 (i.v.) | | |
|  | 100/30 (i.v.) | | |
|  | 2/30 (s.c.) | | |
| 1I | 75 | | |
|  | 8.5 (i.v.) | | |
| 1J | 86 | | |
|  | 6.7 (i.v.) | | |
| 1K | 255 | | |
|  | 1-0/1 (i.v.) | | |
|  | 30/3 (i.v.) | | |
|  | 25/5.5 (i.v.) | | |
|  | 44/10 (i.v.) | | |
| 1M | 50/100 | | |
| 1N | 35.8 | | |
| 1-O | 91.6 | | |
| 1P | 40/100 | | |
|  | 4.5 (i.v.) | | |
| 1Q | 7/24 | | |
|  | 27/79 | | |
|  | 60/238 | | |
|  | 67/435 | | |
|  | 60/793 | | |
|  | 67/1000 | | |
| 1R | 198 | | |
| 1S | 40 | 162 | |
|  | 10/1 (i.v.) | | |
|  | 20/3 (i.v.) | | |
|  | 100/10 (i.v.) | | |
| 1T | 106 | | |
|  | 3.8 (i.v.) | | |
| 1U | 155 | | |
| 1V | 20/300 | | |
| 1W | 0/30 | | |
|  | 40/300 | | |
|  | 47/550 | | |
|  | 10/1 (i.v.) | | |
|  | 0/1.73 (i.v.) | | |
|  | 86/3 (i.v.) | | |
| 1X | 7/300 | | |
| 1Y | 30/100 | | |
| 1Z | 68 | | |
| 1AA | 10/100 | | |
| 1AB | 47/300 | | |
| 1AC | 30 | 0/200 | 43/30 |
|  | 10/1.77 (i.v.) | | 57/50 |
|  | 10/2./2 (i.v.) | | 75/100 |
|  | 80/3 (i.v.) | | |
|  | 100/10 (i.v.) | | |
| 1AE | 29 | 20/300 | 66.2 |
| 1AF | 200 | | |
|  | 0/3 (i.v.) | | |
|  | 0/10 (i.v.) | | |
|  | 30/30 (i.v.) | | |
| 1AG | 40/100 | | |
|  | 47/300 | | |
|  | 10/10 (i.v.) | | |
|  | 56/30 (i.v.) | | |
|  | 20/30 (s.c.) | | |
| 1AH | 85 | | |
| 1AI | 74 | | |
| 1AJ | 13/100 | | |
|  | 53/300 | | |
| 1AK | 40/300 | | |
|  | 47/550 | | |
| 1AL | 113 | | |
| 1AM | 32 | | |
|  | 5 (i.v.) | | |
| 1AO | 28 | 111 | 75/100 |
| 1AP | 42 | 0/50 | |
|  | | 33/200 | |
|  | | 60/400 | |
| 1AQ | 53/300 | | 0/10 |
|  | 17 (i.v.) | | 12/30 |
|  | | | 12/100 |
| 1AR | 27/150 | | |
|  | 27/300 | | |
|  | 13/25 (s.c.) | | |
| 1AS | 33/300 | | |
| 1AT | 30 | 0/50, 200 | |
| 1AU | 42 | 0/50 | |
| 1AV | 38 | 0/50 | |
| 1AW | 6,28,30,43 | 229 | 26 |
| 1AX | 45 | 0/212 | |
| 1AY | 11,37,49 | 141 | 0/30,100 |
|  | 8.5 (i.v.) | | 20/300 |
| 1AZ | 10,27,50 | | |
|  | 20/75 | | |
|  | 73/100 | | |
|  | 53/150 | | |
| 1BA | 197 | | |
| 1BB | 97 | | |
| 1BC | 40/100 | | |
| 1BD | 65 | | |
| 1BE | 50.9 | | |

TABLE B-continued

| Example | Ach | BRDK | P.F. |
|---|---|---|---|
| 1BF | 0/30 | | |
| 1BG | 33/300 | | |
| 1BH | 0/30 | | |
| | 27/100 | | |
| | 53/300 | | |
| | 58/550 | | |
| | 7/30 (s.c.) | | |
| | 50/10 (i.v.) | | |
| 1BI | 13/300 | 0/6 | |
| | 27/100 (s.c.) | | |
| | 0.69 (i.v.) | | |
| 1BJ | 0/100 | | |
| 1BL | 0/100 | | |
| 1BM | 0/100 | | |
| 1BN | 36 | | |
| 1BO | 173 | | |
| 1BP | 28 | | |
| 1BR | 123 | | |
| 1BT | 90/100 | | |
| 1BW | 10/100 | | |
| 1BZ | 0/100 | | |
| 1CA | 20/100 | | |
| 1CB | 60/100 | | |
| 1CC | 10/100 | | |
| 1CD | 79 | | |
| 1CE | 0/100 | | |
| 1CF | 24 | | |
| 1CG | 46.3 | | |
| 1CH | 105 | | |
| 1CI | 70/100 | | |
| 1CJ | 56 | | |
| 1CK | 30/100 | | |
| 1CL | 30/100 | | |
| 2A | 7/30 | | |
| | 60/300 | | |
| | 73/550 | | |
| | 67/1000 | | |
| 2B | 47/300 | | |
| | 33/550 | | |
| 2C | 19,33 | 0/30 | |
| | 3.3 (i.v.) | 60/300 | |
| 2D | 20/100 | | |
| | 40/300 | | |
| | 67/1000 | | |
| 2E | 33 | | |
| 2F | 20/30 | | |
| | 40/100 | | |
| | 33/300 | | |
| 2G | 42 | | |
| 2H | 49 | | |
| 2I | 28 | 132 | 62/100 |
| | 2.6 (i.v.) | | |
| | 18 (s.c.) | | |
| 2J | 60 | | |
| 2L | 10/100 | | |
| 2M | 20/100 | | |
| 2N | 20/100 | | |
| 2-O | 20/100 | | |
| 2P | 30/100 | | |
| 2Q | 20/100 | | |
| 2R | 10/100 | | |
| 2S | 0/100 | | |
| 2T | 30/100 | | |
| 2U | 88 | | |
| 2V | 20/100 | | |
| 2W | 72 | | |
| 2AB | 91 | | |
| 2AC | 30/100 | | |
| 2AD | 10/100 | | |
| 2AE | 20/100 | | |
| 2AF | 30/100 | | |
| 2AG | 143 | | |
| 2AH | 20/100 | | |
| 2AK | 30/0.3 (i.v.) | | |
| 2AL | 20/0.1 (i.v.) | | |
| 2AM | 80/100 | | |
| 2AN | 90 | | |
| 2AO | 40/100 | | |
| 2AP | 27 | | |
| 2AR | 50/100 | | |
| 2AT | 20/100 | | |
| 2AU | 30/100 | | |
| 2AV | 10/100 | | |
| 2AW | 20/100 | | |
| 2AX | 0/100 | | |
| 2AZ | 26 | | |
| 2BB | 40/100 | | |
| 2BC | 10/100 | | |
| 2BD | 15 | | |
| 2BE | 30/100 | | |
| 2BF | 30/100 | | |
| 3A | 68.1 | | |
| 3B | 26.5 | | 50/30 |
| | 10 (s.c.) | | 86/100 |
| | 3 (i.v.) | | 86/300 |
| 3C | 53 | | |
| 3H | 9.7 (i.v.) | | |
| 3-I | 30/100 | | |
| 3J | 30/10 (i.v.) | | |
| 3K | 45.7 | | |
| 3L | 44 | | |
| 3M | 10/100 | | |
| 3N | 40/100 | | |
| 3-O | 76 | | |
| 3P | 71 | | |
| 3Q | 40/100 | | |
| 3R | 40/100 | | |
| 3S | 40/100 | | |
| 3T | 53 | | |
| 3U | 30/100 | | |
| 3V | 253.8 | | |
| 3W | 49 | | |
| 3Y | 69 | | |
| 3AA | 22 | | |
| 3AB | 25 | | |
| 3AC | 21 | | |
| 3AD | 100/100 | | |
| 3AF | 138.6 | | |
| 3AG | 42 | | |
| 3AH | 30/100 | | |
| 3AJ | 35 | | |
| 4A | 16 | 53 | 0.12/100 |
| 4B | 24,25,21,15 | 38,28,19 | 27.6 |
| | 6 (i.v.) | | |
| 4C | 37 | | |
| 4D | 24 | | |
| 5A | 31 | 0/300 | |
| | 20/1 (i.v.) | | |
| | 29/3 (i.v.) | | |
| | 30/10 (i.v.) | | |
| 5B | 25 | 61 | 0/10 |
| | | | 12/30 |
| | | | 12/100 |
| 5C | 19 | 20/30 | |
| | 60/100 | | |
| | 60/300 | | |
| 5D | 84 | 20/200 | |
| | 57/3 (i.v.) | | |
| | 29/1 (i.v.) | | |
| 5E | 38/150 | | |
| | 40/300 | | |
| 5F | 76 | | |
| 6 | 83 | 0/100 | |
| | 0/10 (i.v.) | 0/300 | |
| | 0/30 (i.v.) | | |
| | 13/30 (s.c.) | | |
| 7 | 40 | 0/300 | |
| 8A | 32 | | 62/30 |
| 8B | 35/100 | | |
| 9 | 27/300 | | |
| | 20/30 (s.c.) | | |
| 10 | 0/30 | | |
| | 7/30 (s.c.) | | |
| 11 | 20/30 | | |
| | 13/30 (s.c.) | | |
| 12 | 13/30 | | |
| | 0/30 | | |
| 13A | 139 | | |
| 13B | 0/100 | | |
| 13C | 20/100 | | |
| 14 | 40/100 | | |
| 15 | 155 | | |

TABLE B-continued

| Example | Ach | BRDK | P.F. |
|---|---|---|---|
| 16A | 10/100 | | |
| 16B | 20/100 | | |
| 17 | 7/30 | 33/100 (s.c.) | |
| | 6.6 (s.c.) | | |
| 18 | 30/100 | | |
| 19 | 40/100 | | |
| 20A | 128 | | |
| 20B | 40/100 | | |
| 21 | 31 | | |
| 22 | 66.8 | | |
| 23A | 85 | | |
| 23B | 39 | | |
| 25A (r) | 82.5 | | |
| 25B | 42 | | |
| 26A | 40/100 | | |
| 26B | 40/100 | | |
| 26C | 30/100 | | |
| 26D | 30/100 | | |
| 26E | 73.1 | | |
| 26F | 61 | | |
| 26G | 20/100 | | |
| 27A | 20.7 | | |
| 27B | 59.8 | | |
| 27C | 29.4 | | |
| 27D | 30 | | |
| 28 | 90/100 | | |
| 29A | 60,80/100 | | |
| 29B | 60,70/100 | | |
| 29C | 0/100 | | |
| 30 | 10/100 | | |
| 31A | 58 | | |
| 31C | 53 | | |
| 31F | 0/3 (i.v.) | | |
| 31G | 133 | | |
| 31H | 56 | | |
| | 30/100 (i.c.v.) | | |
| | 80/10 (i.v.) | | |
| 31-I | 31,40,88/100 | | |
| 31J | 10/100 | | |
| 31K | 28 | | |
| 31L | 32 | | |
| 31M | 26 | | |
| 31N | 90,100/100 | | |
| 31-O | 100/100 | | |
| 32 | 85 | | |
| 33 | 20/100 | | |

(r) N=B is amino

The 3-R$_3$-carbonyl-1-aminoalkyl-1H-indoles of formulas I, Ia and Ib of the invention were also tested in the developing adjuvant arthritic assay, the plasma fibronectin assay and the pleurisy macrophage assay in rats. Data so-obtained, expressed as p-values as a measure of the statistical significant of the results for each of the parameters measured, i.e. inhibition of inflammation of non-injected paw (NIP) and injected paw (right pay volume or RPV), lowering of plasma fibronectin levels (FN) and inhibition of macrophage accumulation in the pleural cavity (MAC), are given in Table C. Compounds were considered active at p≦0.05 levels. Non-statistically significant results as "—".

TABLE C

| Example | NIP | RPV | FN | MAC |
|---|---|---|---|---|
| 1B (s) | 0.01 | 0.01 | — | |
| 1F | 0.01 | 0.01 | — | |
| 1I | 0.01 | 0.01 | 0.01 | 0.01 |
| 1U | — | — | — | |
| 1AC | | | | |
| 1AO | — | — | — | |
| 1AP | — | — | — | |
| 1AW | | | — | |
| 1BA | — | — | 0.01 | |
| 1BB | — | — | — | |
| 1BD | — | — | — | |
| 1BE | — | 0.05 | — | |
| 1BL | 0.01 | 0.05 | 0.01 | |
| 1BM | 0.01 | 0.01 | 0.01 | 0.01 |
| 1BN | | | | — |
| 1BO | — | 0.01 | 0.05 | |
| 1BP | 0.01 | 0.01 | — | |
| 1BQ (t) | 0.01 | 0.01 | 0.01 | 0.01 |
| 1BR | 0.01 | 0.01 | 0.01 | — |
| 1BZ | 0.05 | 0.01 | 0.01 | — |
| 1CC | — | — | — | |
| 1CE | — | — | — | |
| 1CF | 0.01 | 0.01 | — | |
| 1CG | 0.01 | 0.01 | 0.01 | — |
| 1CH | — | — | — | |
| 1CJ | 0.01 | 0.01 | — | — |
| 1CL | — | — | 0.01 | |
| 1CM | — | 0.01 | — | — |
| 1CO | 0.01 | 0.01 | — | |
| 1CP | 0.01 | 0.01 | 0.01 | 0.01 |
| 2C | 0.01 | 0.01 | 0.01 | 0.01 |
| 2E | 0.01 | 0.01 | — | — |
| 2R | — | — | — | |
| 2S | — | — | — | |
| 2U | — | — | 0.01 | |
| 2V | — | — | — | |
| 2Y | 0.05 | — | — | |
| 2AA | — | — | — | |
| 2AB | — | — | — | |
| 2AC | 0.05 | — | — | |
| 2AD | — | — | — | |
| 2AE | 0.01 | 0.01 | — | |
| 2AF | 0.01 | 0.01 | — | |
| 2AG | 0.01 | — | 0.01 | |
| 2AI | 0.01 | 0.01 | 0.01 | |
| 2AK | — | — | — | |
| 2AN | — | — | — | |
| 2AO | 0.01 | 0.01 | 0.01 | 0.05 |
| 2AQ | | | | — |
| 2AS | — | — | — | |
| 2AT | — | — | — | |
| 2AU | — | — | 0.05 | |
| 2AV | — | — | — | — |
| 2AW | — | — | — | 0.05 |
| 2AX | — | — | — | — |
| 2AY | 0.01 | 0.05 | — | |
| 2BB | — | 0.01 | 0.05 | |
| 2BF | — | 0.01 | 0.01 | |
| 3D | — | — | — | |
| 3E | 0.01 | — | — | |
| 3F | 0.05 | 0.01 | — | |
| 3G | — | — | — | |
| 3K | — | 0.01 | 0.05 | |
| 3T | — | 0.01 | — | — |
| 3U | — | — | — | |
| 3W | 0.01 | 0.01 | 0.05 | |
| 3AF | — | 0.01 | — | |
| 3AG | 0.01 | 0.01 | 0.01 | — |
| 3AH | 0.01 | — | 0.01 | |
| 3AI | 0.01 | 0.01 | 0.05 | |
| 3AJ | 0.01 | 0.01 | 0.05 | |
| 6 | — | — | 0.05 | |
| 13B | — | — | 0.01 | |
| 13C | — | — | — | |
| 16A | 0.05 | — | — | |
| 19 | — | — | — | |
| 20A | — | — | 0.05 | |
| 20B | — | — | — | |
| 21 | — | — | — | |
| 22 | 0.01 | 0.01 | — | 0.05 |
| 23A | 0.01 | 0.01 | 0.01 | — |
| 23B | 0.01 | 0.01 | 0.01 | |
| 24 | 0.05 | 0.01 | — | |
| 25A | | | | — |
| 25B | — | — | — | |
| 26E | — | — | — | |
| 26F | 0.05 | 0.01 | — | |
| 26G | — | — | 0.01 | — |
| 27A | 0.05 | 0.01 | — | |
| 27B | 0.05 | 0.01 | — | |
| 27D | 0.01 | 0.01 | — | |
| 29A | 0.05 | 0.01 | — | |
| 29B | | | | — |

TABLE C-continued

| Example | NIP | RPV | FN | MAC |
|---|---|---|---|---|
| 31A | 0.01 | | 0.01 | — |
| 31B | 0.01 | — | | |
| 31H | 0.01 | | — | |
| 31J | 0.05 | | — | |
| 31L | 0.05 | 0.01 | — | — |
| 31M | 0.01 | | — | 0.01 |
| 31N | 0.01 | 0.01 | — | — |
| 31-O | 0.01 | 0.01 | — | — |
| 32 | 0.01 | 0.01 | 0.05 | |

(s) The maleate salt
(t) The lower melting polymorph

Certain species of the intermediate 2-$R_2$-3-($R_3$-carbonyl)-indoles of formula II were also tested and found active in one or more of the acetylcholine-induced abdominal construction test (Ach), the developing adjuvant arthritic assay (NIP and RPV), the fibronectin assay FN) and the pleurisy macrophage assay MAC). Data so-obtained, expressed as described above, are given in Table D.

TABLE D

| Prepn. | Ach | NIP | RPV | FN | MAC |
|---|---|---|---|---|---|
| 1F | 0/100 | — | — | — | — |
| 1AJ | | | | | |
| 1AK | 20/100 | — | — | — | 0.05 |
| 1AL | 20/100 | 0.01 | — | 0.01 | 0.01 |
| 1AM | | — | — | 0.01 | |
| 1AN | | 0.01 | 0.01 | — | — |
| 1AO | 40/100 | | | | |
| 1AQ | | 0.01 | 0.01 | 0.01 | |

Certain species of the intermediate 2-$R_2$-1-aminoalkyl-1H-indoles of formula III were tested and found active in the acetylcholine-induced abdominal constriction test. Thus 2-methyl-1-[1-methyl-2-(4-morpholinyl)ethyl]-1H-indole methanesulfonate hydrate (Preparation 5A) produced 40% inhibition at 300 mg./kg. (p.o.), and the $ED_{50}$ of 5-fluoro-2-methyl-1-(1-methyl-2dimethylaminoethyl)-1H-indole (Preparation 8) was found to be 25 mg./kg/ (p.o.).

I claim:

1. A compound having the formula:

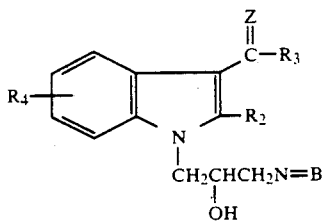

wherein:
$R_2$ is hydrogen, lower-alkyl, chloro, phenyl or benzoyl (or phenyl or benzoyl substituted by from one to two substituents selected from halo, lower-alkyl, lower-alkoxy, hydroxy, amino, lower-alkylmercapto, lower-alkylsulfinyl or lower-alkylsulfonyl);
$R_3$ is cyclohexyl, lower-alkoxycyclohexyl, phenyl (or phyenyl substituted by from one to two substituents selected from halo, lower-alkoxy, hydroxy, benzyloxy, lower-alkyl, nitro, amino, lower-alkylamino, di-lower-alkylamino, lower-alkoxy-lower-alkylamino, lower-alkanoylamino, benzoylamino, trifluroracetylamino, lower-alkyl-sulfonylamino, carbamylamo, lower-alkylmercapto, lower-alkylsulfinyl, lower-alkylsulfonyl, cyano, formyl and oximinomethylene), methylenedioxyphenyl, 3- or 4-hydroxy-1-piperidinylphenyl, 1-piperazinylphenyl, (1H-imidazol-1-yl)phenyl, (1-pyrrolyl)phenyl, aminomethylphenyl, guanidinylmethylphenyl, N-cyanoguanidinylmethylphenyl, styryl, lower-alkyl-substituted-styryl, fluorosubstituted-styryl, 2- or 4-biphenyl, 1- or 2-naphthyl (or1- or 2-naphthyl substituted by from one to two substituents selected from lower-alkyl, lower alkoxy, hydroxy, bromo, chloro, fluoro, lower-alkoxycarbonyl, carbamyl, cyano, lower-alkyl-mercapto, lower-alkylsulfinyl, lower-alkylsulfonyl and trifluoromethyl), thienyl, furyl, benzofuryl, benzothienyl, quinolyl, or (N-lower-alkyl)pyrrolyl;
$R_4$ is hydrogen or from one to two substituents selected from lower-alkyl, hydroxy, lower-alkoxy and halo in the 4-, 5-, 6- or 7-positions;
C=Z is C=O or C=NOH; and
N=B is azido, amino, N-lower-alkylamino, N,N-dilower-alkylamino, N-(hydroxy-lower-alkyl)amino, N,N-di-(hydroxy-lower-alkyl)amino, N-lower-alkyl-N-(hydroxy-lower-alkyl)amino, N-(lower-alkoxy-lower-alkyl)amino, N-(halo-n-propyl)amino, 4-morpholinyl, 2-lower-alkyl-4-morpholinyl, 2,6-di-lower-alkyl-4-morpholinyl, 4-thiomorpholinyl, 4-thiomorpholinyl-S-oxide, 4-thiomorpholinyl-S,S-dioxide, 1-piperidinyl, 3-or 4-hydroxy-1-piperidinyl, 3- or 4-lower-alkanoyloxy-1-piperidinyl, 3- or 4-amino-1-piperidinyl, 3- or 4-(N-lower-alkanoylamino)-1-piperidinyl, 2-cyclohexylmethyl-1-piperidinyl, 1pyrrolidinyl, 3-hydroxy-1-pyrrolidinyl, 1-azetidinyl, 1-piperazinyl, 4-lower-alkyl-1piperazinyl, 4-lower-alkanoyl-1-piperazinyl, 4-carbo-lower-alkoxy-1-piperazinyl, hexahydro-4H-1,4-diazepin-4-yl or the N=BN-oxides thereof; or an acid addition salt thereof.

2. A compound according to claim 1 wherein:
$R_2$ is lower-alkyl;
$R_3$ is lower-alkoxy-substituted phenyl or 1-naphthyl;
$R_4$ is hydrogen or halogen;
C=Z is C=O; and
N=B is azido, amino, N-lower-alkylamino, N,N-dilower-alkylamino, 4-morpholinyl, 1-piperidinyl, 1-pyrrolidinyl or 1 -azetidinyl; or an acid-addition salt thereof.

3. A compound according to claim 2 wherein $R_4$ is fluoro.

4. 1-[2-Hydroxy-3-(4-morpholinyl)propyl]-5-fluoro-2-methyl-3-(4-methoxybenzoyl)-1H-indole or an acid-addition salt thereof according to claim 3, 5. An analgesic, anti-rheumatic or anti-inflammatory composition for the relief of pain or rheumatic or inflammatory conditions which comprises a pharmaceutically acceptable carrier and, as the active component thereof, an effective analgesic, anti-rheumatic or anti-inflammatory amount of a compound according to claim 1.

6. A method for the relief of pain or rheumatic or inflammatory conditions in a patient requiring such treatment which comprises administering orally or parenterally to such patient a medication in solid or liquid dosage form containing, as the active component thereof, an effective analgesic, anti-rheumatic or anti-inflammatory amount of a compound according to claim 1.

* * * * *

UNITED STATES PATENT AND TRADEMARK OFFICE
CERTIFICATE OF CORRECTION

PATENT NO. : 5,013,732
DATED     : May 7, 1991
INVENTOR(S) : Malcolm R. Bell

It is certified that error appears in the above-identified patent and that said Letters Patent is hereby corrected as shown below:

Column 16, line 1m, "75" should read --62--;
            line 1m, "220-220/iPrOH" should read
                    --218-220/i-PrOH--.

Column 34, line 3X, "HCl.1/2H$_2$O" should read
                    --HCl.1/4H$_2$O--.

Column 35, line 16, "28 9" should read
            --28 g--.

Column 45, line 50, "12.4" should read
            --13.4--.

Column 50, TABLE B, "60/100 and 60/300"
            should be located in BRDK column
            instead of Ach column.

Column 53, lines 55-56, "benzoyl" should be
            --benzyl--(two occurrences); line 61,
            "phyenyl" should be --phenyl--;

Signed and Sealed this

Ninth Day of February, 1993

Attest:

STEPHEN G. KUNIN

Attesting Officer

Acting Commissioner of Patents and Trademarks